US 7,749,524 B2
Jul. 6, 2010

(12) United States Patent
Lu et al.

(10) Patent No.: US 7,749,524 B2
(45) Date of Patent: Jul. 6, 2010

(54) COSMETIC COMPOSITIONS COMPRISING A STRUCTURING AGENT, SILICONE POWDER AND SWELLING AGENT

(75) Inventors: Shao Xiang Lu, Plainsboro, NJ (US); Terry Van Liew, Cranford, NJ (US); Nathalie Geffroy-Hyland, Franconville (FR); Mohamed Kanji, Edison, NJ (US)

(73) Assignee: L'Oreal S.A. (FR)

( * ) Notice: Subject to any disclaimer, the term of this patent is extended or adjusted under 35 U.S.C. 154(b) by 105 days.

(21) Appl. No.: 10/746,612

(22) Filed: Dec. 22, 2003

(65) Prior Publication Data
US 2005/0008599 A1 Jan. 13, 2005

Related U.S. Application Data

(63) Continuation of application No. 10/618,315, filed on Jul. 11, 2003, now abandoned.

(51) Int. Cl.
*A61Q 1/00* (2006.01)
*A61Q 1/06* (2006.01)
*A61Q 1/08* (2006.01)
*A61Q 1/12* (2006.01)

(52) U.S. Cl. ................... 424/401; 424/64; 424/69; 424/70.1; 424/70.7

(58) Field of Classification Search ............. 424/401, 424/63, 64, 69, 78.17
See application file for complete search history.

(56) References Cited

U.S. PATENT DOCUMENTS

| 2,379,413 | A | 7/1945 | Bradley |
| 2,450,940 | A | 10/1948 | Cowan et al. |
| 2,463,264 | A | 3/1949 | Graenacher |
| 2,662,068 | A | 12/1953 | Floyd |
| 2,663,649 | A | 12/1953 | Winkler |
| 2,890,097 | A | 6/1959 | Coe |
| 2,962,461 | A | 11/1960 | Toussaint et al. |
| 3,086,914 | A | 4/1963 | Soloway |
| 3,141,787 | A | 7/1964 | Goetze et al. |
| 3,148,125 | A | 9/1964 | Strianse et al. |
| 3,156,572 | A | 11/1964 | Carlick et al. |
| 3,157,681 | A | 11/1964 | Fischer |
| 3,255,082 | A | 6/1966 | Barton |
| 3,324,041 | A | 6/1967 | Sommer et al. |
| 3,341,465 | A | 9/1967 | Kaufman et al. |
| 3,412,115 | A | 11/1968 | Floyd et al. |
| 3,615,289 | A | 10/1971 | Felton |
| 3,645,705 | A | 2/1972 | Miller et al. |
| 3,778,394 | A | 12/1973 | Lovald et al. |
| 3,819,342 | A | 6/1974 | Gunderman et al. |
| 3,857,960 | A | 12/1974 | Mackles |
| 3,926,655 | A | 12/1975 | Miles |
| 3,937,811 | A | 2/1976 | Papantoniou et al. |
| 3,969,087 | A | 7/1976 | Saito et al. |
| 4,049,792 | A | 9/1977 | Elsnau |
| 4,051,159 | A | 9/1977 | Tsoucalas et al. |
| 4,062,819 | A | 12/1977 | Mains et al. |
| RE29,871 | E | 12/1978 | Papantoniou et al. |
| 4,128,436 | A | 12/1978 | O'Hara et al. |
| 4,137,306 | A | 1/1979 | Rubino et al. |
| 4,148,875 | A | 4/1979 | Barnett et al. |
| 4,150,002 | A | 4/1979 | Drawert et al. |
| 4,247,411 | A | 1/1981 | Vanlerberghe et al. |
| 4,275,054 | A | 6/1981 | Sebag et al. |
| 4,275,055 | A | 6/1981 | Nachtigal et al. |
| 4,278,658 | A | 7/1981 | Hooper et al. |
| 4,279,658 | A | 7/1981 | Harvey et al. |
| 4,337,298 | A | 6/1982 | Karim et al. |
| 4,341,671 | A | 7/1982 | Bolze et al. |
| 4,367,390 | A | 1/1983 | Balleys et al. |
| 4,376,194 | A | 3/1983 | Tanaka et al. |
| 4,387,090 | A | 6/1983 | Bolich, Jr. |
| 4,438,240 | A | 3/1984 | Tanaka et al. |
| 4,466,936 | A | 8/1984 | Schapel |
| 4,536,405 | A | 8/1985 | Nara et al. |
| 4,552,693 | A | 11/1985 | Hussain et al. |
| 4,571,267 | A | 2/1986 | Drawert et al. |
| 4,620,492 | A | 11/1986 | Vogg et al. |
| 4,655,836 | A | 4/1987 | Drawert et al. |
| 4,663,428 | A | 5/1987 | Okitu et al. |
| 4,699,779 | A | 10/1987 | Palinczar |
| 4,699,924 | A | 10/1987 | Durrant et al. |
| 4,712,571 | A | 12/1987 | Remz et al. |
| 4,724,137 | A | 2/1988 | Hoppe et al. |

(Continued)

FOREIGN PATENT DOCUMENTS

CA 2003346 5/1990

(Continued)

OTHER PUBLICATIONS

Bush Boake Allen, Inc., Uniclear Formulations, dated Oct. 13, 1998.

(Continued)

*Primary Examiner*—Jyothsna A Venkat
(74) *Attorney, Agent, or Firm*—Finnegan, Henderson, Farabow, Garrett & Dunner, L.L.P.

(57) ABSTRACT

Disclosed are compositions that include a structuring agent, a silicone powder and a swelling agent, other compositions further including a liquid fatty phase, methods of making the compositions, and their use on keratin material.

79 Claims, No Drawings

U.S. PATENT DOCUMENTS

| | | |
|---|---|---|
| 4,769,285 A | 9/1988 | Rasmussen |
| 4,806,338 A | 2/1989 | Smith |
| 4,806,345 A | 2/1989 | Bhattacharyya |
| 4,820,765 A | 4/1989 | Whyzmuzis |
| 4,822,601 A | 4/1989 | Goode et al. |
| 4,871,536 A | 10/1989 | Arraudeau et al. |
| 4,885,709 A | 12/1989 | Edgar et al. |
| 4,937,069 A | 6/1990 | Shin |
| 4,952,245 A | 8/1990 | Iwano et al. |
| 5,034,219 A | 7/1991 | Deshpande et al. |
| 5,061,289 A | 10/1991 | Clausen et al. |
| 5,069,897 A | 12/1991 | Orr |
| 5,073,364 A | 12/1991 | Giezendanner et al. |
| 5,075,103 A | 12/1991 | Halloran et al. |
| 5,085,859 A | 2/1992 | Halloran et al. |
| 5,102,656 A | 4/1992 | Kasat |
| 5,126,136 A | 6/1992 | Merat et al. |
| 5,166,355 A | 11/1992 | Leistner et al. |
| 5,186,318 A | 2/1993 | Oestreich et al. |
| 5,194,260 A | 3/1993 | Grollier et al. |
| 5,196,260 A | 3/1993 | Dirschl et al. |
| 5,223,559 A | 6/1993 | Arraudeau et al. |
| 5,237,071 A | 8/1993 | Leistner et al. |
| 5,252,323 A | 10/1993 | Richard et al. |
| 5,268,029 A | 12/1993 | Demangeon et al. |
| 5,272,241 A | 12/1993 | Lucarelli et al. |
| 5,290,555 A | 3/1994 | Guthauser et al. |
| 5,302,379 A | 4/1994 | Sojka |
| 5,302,398 A | 4/1994 | Egidio et al. |
| 5,342,894 A | 8/1994 | Robeson et al. |
| 5,356,616 A | 10/1994 | Sojka |
| 5,362,482 A | 11/1994 | Yoneyama et al. |
| 5,372,852 A | 12/1994 | Titterington et al. |
| 5,389,363 A | 2/1995 | Snyder et al. |
| 5,436,006 A | 7/1995 | Hirose et al. |
| 5,472,686 A | 12/1995 | Tsubaki et al. |
| 5,486,431 A | 1/1996 | Tuttle et al. |
| 5,489,431 A | 2/1996 | Ascione et al. |
| 5,500,209 A | 3/1996 | Ross et al. |
| 5,505,937 A | 4/1996 | Castrogiovanni et al. |
| 5,510,452 A | 4/1996 | Santhanam |
| 5,534,247 A | 7/1996 | Franjac et al. |
| 5,536,871 A | 7/1996 | Santhanam |
| 5,538,718 A | 7/1996 | Aul et al. |
| 5,538,793 A | 7/1996 | Inokuchi et al. |
| 5,540,853 A | 7/1996 | Trinh et al. |
| 5,585,091 A | 12/1996 | Pelzer et al. |
| 5,603,925 A | 2/1997 | Ross et al. |
| 5,605,651 A | 2/1997 | Balzer |
| 5,610,199 A | 3/1997 | Cohen et al. |
| 5,612,043 A | 3/1997 | Deprez et al. |
| 5,616,331 A | 4/1997 | Allard et al. |
| 5,618,523 A | 4/1997 | Zysman et al. |
| 5,620,693 A | 4/1997 | Piot et al. |
| 5,645,632 A | 7/1997 | Pavlin |
| 5,667,770 A | 9/1997 | Szweda et al. |
| 5,679,357 A | 10/1997 | Dubief et al. |
| 5,683,817 A | 11/1997 | Kenmochi |
| 5,695,747 A | 12/1997 | Forestier et al. |
| 5,702,519 A | 12/1997 | Nitta et al. |
| 5,708,631 A | 1/1998 | Takenaka et al. |
| 5,719,255 A | 2/1998 | Heucher et al. |
| 5,733,537 A | 3/1998 | Halloran et al. |
| 5,747,625 A | 5/1998 | Furukawa et al. |
| 5,750,125 A | 5/1998 | Lahanas et al. |
| 5,750,127 A | 5/1998 | Rokitowski |
| 5,750,489 A | 5/1998 | Garcia et al. |
| 5,769,902 A | 6/1998 | Samain |
| 5,780,517 A | 7/1998 | Cohen et al. |
| 5,783,657 A | 7/1998 | Pavlin et al. |
| 5,795,565 A | 8/1998 | Eteve et al. |
| 5,800,816 A | 9/1998 | Brieva et al. |
| 5,807,968 A | 9/1998 | Heinrich et al. |
| 5,825,543 A | 10/1998 | Ouderkirk et al. |
| 5,830,444 A | 11/1998 | Miguel |
| 5,830,447 A | 11/1998 | Hutchins et al. |
| 5,830,483 A | 11/1998 | Seidel et al. |
| 5,837,223 A | 11/1998 | Barone et al. |
| 5,849,275 A | 12/1998 | Calello et al. |
| 5,849,278 A | 12/1998 | Piot et al. |
| 5,849,333 A | 12/1998 | Nordhauser et al. |
| 5,849,909 A | 12/1998 | Richard et al. |
| 5,851,517 A | 12/1998 | Mougin et al. |
| 5,857,903 A | 1/1999 | Ramspeck et al. |
| 5,858,338 A | 1/1999 | Piot et al. |
| 5,866,149 A | 2/1999 | Piot et al. |
| 5,871,758 A | 2/1999 | Nagy et al. |
| 5,871,764 A | 2/1999 | Diaz et al. |
| 5,874,069 A | 2/1999 | Mendolia et al. |
| 5,882,363 A | 3/1999 | Spaulding et al. |
| 5,891,424 A | 4/1999 | Bretzler et al. |
| 5,897,869 A | 4/1999 | Roulier et al. |
| 5,902,592 A | 5/1999 | Bara et al. |
| 5,908,631 A | 6/1999 | Arnaud et al. |
| 5,911,974 A | 6/1999 | Brieva et al. |
| 5,919,441 A | 7/1999 | Mendolia et al. |
| 5,925,337 A | 7/1999 | Arraudeau et al. |
| 5,928,660 A | 7/1999 | Kobayashi et al. |
| 5,945,095 A | 8/1999 | Mougin et al. |
| 5,945,112 A | 8/1999 | Flynn et al. |
| 5,955,060 A | 9/1999 | Huglin et al. |
| 5,959,009 A | 9/1999 | Konik et al. |
| 5,961,998 A | 10/1999 | Arnaud et al. |
| 5,962,452 A | 10/1999 | Haase et al. |
| 5,965,112 A * | 10/1999 | Brieva et al. .................. 424/64 |
| 5,972,095 A | 10/1999 | Graves et al. |
| 5,972,354 A | 10/1999 | de la Poterie et al. |
| 5,972,359 A | 10/1999 | Sine et al. |
| 5,976,512 A | 11/1999 | Huber |
| 5,976,514 A | 11/1999 | Guskey et al. |
| 5,981,680 A | 11/1999 | Petroff et al. |
| 5,985,298 A | 11/1999 | Brieva et al. |
| 5,993,787 A | 11/1999 | Sun et al. |
| 5,998,570 A | 12/1999 | Pavlin et al. |
| 6,001,980 A | 12/1999 | Borzo et al. |
| 6,004,567 A | 12/1999 | Marchi-Lemann et al. |
| 6,007,796 A | 12/1999 | Menzel et al. |
| 6,007,799 A | 12/1999 | Lee et al. |
| 6,010,541 A | 1/2000 | de la Mettrie et al. |
| 6,019,962 A | 2/2000 | Rabe et al. |
| 6,036,947 A | 3/2000 | Barone et al. |
| 6,042,815 A | 3/2000 | Kellner et al. |
| 6,045,782 A | 4/2000 | Krog et al. |
| 6,045,823 A | 4/2000 | Vollhardt et al. |
| 6,051,216 A | 4/2000 | Barr et al. |
| 6,054,517 A | 4/2000 | Spaulding et al. |
| 6,060,072 A | 5/2000 | Konik et al. |
| 6,063,398 A | 5/2000 | Gueret |
| 6,066,328 A | 5/2000 | Ribier et al. |
| 6,074,654 A | 6/2000 | Drechsler et al. |
| 6,093,385 A | 7/2000 | Habeck et al. |
| 6,103,249 A | 8/2000 | Roulier et al. |
| 6,103,250 A | 8/2000 | Brieva et al. |
| 6,106,820 A | 8/2000 | Morrissey et al. |
| 6,111,055 A | 8/2000 | Berger et al. |
| 6,126,929 A | 10/2000 | Mougin |
| 6,132,745 A | 10/2000 | Marchi-Lemann et al. |
| 6,156,325 A | 12/2000 | Farer et al. |
| 6,156,804 A | 12/2000 | Chevalier et al. |
| 6,159,455 A | 12/2000 | Habeck et al. |
| 6,165,454 A | 12/2000 | Patel et al. |
| 6,165,971 A | 12/2000 | Oppenlander et al. |
| 6,171,347 B1 | 1/2001 | Kunz |
| 6,177,523 B1 | 1/2001 | Reich et al. |

| | | | | | | |
|---|---|---|---|---|---|---|
| 6,180,117 B1 | 1/2001 | Berthiaume et al. | | 7,052,681 B2 | 5/2006 | Ferrari |
| 6,180,123 B1 | 1/2001 | Mondet | | 7,144,582 B1 | 12/2006 | Ferrari et al. |
| 6,190,673 B1 | 2/2001 | Guskey et al. | | 7,276,547 B2 | 10/2007 | Pinzon et al. |
| 6,197,100 B1 | 3/2001 | Melbouci | | 7,314,612 B2 | 1/2008 | Ferrari |
| 6,203,780 B1 | 3/2001 | Arnaud et al. | | 7,351,418 B2 | 4/2008 | Collin |
| 6,203,807 B1 | 3/2001 | Lemann | | 7,410,636 B2 | 8/2008 | Collin |
| 6,214,326 B1 | 4/2001 | Dupuis | | 2001/0014312 A1 | 8/2001 | Nakanishi et al. |
| 6,214,329 B1 | 4/2001 | Brieva et al. | | 2001/0014313 A1 | 8/2001 | Roulier et al. |
| 6,221,389 B1 | 4/2001 | Cannell et al. | | 2001/0028887 A1 | 10/2001 | Douin et al. |
| 6,224,851 B1 | 5/2001 | Bara | | 2001/0031280 A1 | 10/2001 | Ferrari et al. |
| 6,242,509 B1 | 6/2001 | Berger et al. | | 2001/0033846 A1 | 10/2001 | Roulier et al. |
| 6,251,375 B1 | 6/2001 | Bara | | 2002/0010179 A1 | 1/2002 | Richard et al. |
| 6,251,409 B1 | 6/2001 | Hegyi et al. | | 2002/0044918 A1 | 4/2002 | Bara |
| 6,254,876 B1 | 7/2001 | de la Poterie et al. | | 2002/0058053 A1 | 5/2002 | Nakanishi et al. |
| 6,254,877 B1 | 7/2001 | de la Poterie et al. | | 2002/0081323 A1 | 6/2002 | Nakanishi et al. |
| 6,264,933 B1 | 7/2001 | Bodelin et al. | | 2002/0102225 A1 | 8/2002 | Hess et al. |
| 6,268,466 B1 | 7/2001 | MacQueen et al. | | 2002/0107314 A1 | 8/2002 | Pinzon et al. |
| 6,280,846 B1 | 8/2001 | Darby et al. | | 2002/0111330 A1 | 8/2002 | Pinzon et al. |
| 6,287,552 B1 | 9/2001 | Tournilhac et al. | | 2002/0114771 A1 | 8/2002 | Nakanishi |
| 6,299,979 B1 | 10/2001 | Neubauer et al. | | 2002/0114773 A1 | 8/2002 | Kanji et al. |
| 6,325,994 B1 | 12/2001 | Collin et al. | | 2002/0119171 A1 | 8/2002 | Gruning et al. |
| 6,342,239 B1 | 1/2002 | Tachibana et al. | | 2002/0120036 A1 | 8/2002 | Pinzon et al. |
| 6,348,563 B1 | 2/2002 | Fukuda et al. | | 2002/0122781 A1 | 9/2002 | Pinzon et al. |
| 6,361,764 B2 | 3/2002 | Richard et al. | | 2002/0131947 A1 | 9/2002 | Nakanishi |
| 6,372,235 B1 | 4/2002 | Livoreil et al. | | 2002/0141958 A1 | 10/2002 | Maio et al. |
| 6,376,078 B1 | 4/2002 | Inokuchi | | 2002/0150602 A1 | 10/2002 | Livoreil et al. |
| 6,383,502 B1 | 5/2002 | Dunshee et al. | | 2002/0159964 A1 | 10/2002 | Nakanishi et al. |
| 6,387,498 B1 | 5/2002 | Coulter et al. | | 2002/0168335 A1 | 11/2002 | Collin |
| 6,399,080 B1 | 6/2002 | Bara | | 2002/0172696 A1 | 11/2002 | Ferrari |
| 6,399,081 B1 | 6/2002 | Nakanishi et al. | | 2002/0189030 A1 | 12/2002 | Collin |
| 6,402,408 B1 * | 6/2002 | Ferrari ........................ 401/64 | | 2002/0192168 A1 | 12/2002 | Blin et al. |
| 6,410,003 B1 | 6/2002 | Bhatia et al. | | 2003/0012764 A1 | 1/2003 | Collin |
| 6,419,912 B1 | 7/2002 | Lezer | | 2003/0026772 A1 | 2/2003 | Jager-Lezer et al. |
| 6,423,306 B2 | 7/2002 | Caes et al. | | 2003/0044367 A1 | 3/2003 | Simon et al. |
| 6,423,324 B1 | 7/2002 | Murphy et al. | | 2003/0086883 A1 | 5/2003 | Feng et al. |
| 6,428,773 B1 | 8/2002 | Oko et al. | | 2003/0129211 A9 | 7/2003 | Livoreil et al. |
| 6,432,391 B1 | 8/2002 | Bara | | 2003/0147837 A1 | 8/2003 | Cavazzuti et al. |
| 6,447,759 B2 | 9/2002 | Noguchi et al. | | 2003/0161807 A1 | 8/2003 | Lemann |
| 6,469,131 B2 | 10/2002 | Lawson et al. | | 2003/0161848 A1 | 8/2003 | Ferrari et al. |
| 6,475,500 B2 * | 11/2002 | Vatter et al. ................. 424/401 | | 2003/0185780 A1 | 10/2003 | Ferrari et al. |
| 6,479,686 B2 | 11/2002 | Nakanishi et al. | | 2003/0198613 A1 | 10/2003 | Feng et al. |
| 6,482,400 B1 | 11/2002 | Collin | | 2004/0013625 A1 | 1/2004 | Kanji |
| 6,489,283 B1 | 12/2002 | Afriat | | 2004/0028636 A1 | 2/2004 | Collin |
| 6,491,931 B1 | 12/2002 | Collin | | 2004/0042980 A1 | 3/2004 | Kanji et al. |
| 6,497,861 B1 * | 12/2002 | Wang et al. .................... 424/64 | | 2004/0086478 A1 | 5/2004 | Ferrari |
| 6,503,521 B1 | 1/2003 | Atis et al. | | 2004/0091510 A1 | 5/2004 | Feng et al. |
| 6,503,522 B2 | 1/2003 | Lawson et al. | | 2004/0126401 A1 | 7/2004 | Collin |
| 6,506,716 B1 | 1/2003 | Delplancke et al. | | 2004/0166076 A1 | 8/2004 | Ferrari et al. |
| 6,524,598 B2 | 2/2003 | Sunkel et al. | | 2004/0166133 A1 | 8/2004 | Cavazzuti et al. |
| 6,545,174 B2 | 4/2003 | Habeck et al. | | 2004/0223987 A1 | 11/2004 | Ferrari |
| 6,552,160 B2 | 4/2003 | Pavlin | | 2004/0247549 A1 | 12/2004 | Lu et al. |
| 6,607,734 B1 | 8/2003 | Afriat | | 2005/0008595 A1 | 1/2005 | Duffournier et al. |
| 6,649,173 B1 | 11/2003 | Arnaud et al. | | 2005/0008598 A1 | 1/2005 | Lu et al. |
| 6,656,487 B2 | 12/2003 | Afriat et al. | | 2005/0008599 A1 | 1/2005 | Lu et al. |
| 6,682,748 B1 | 1/2004 | De La Poterie et al. | | 2005/0065261 A1 | 3/2005 | Darlington, Jr. et al. |
| 6,689,345 B2 | 2/2004 | Jager Lezer | | 2005/0089491 A1 | 4/2005 | Collin |
| 6,716,420 B2 * | 4/2004 | Feng et al. .................. 424/70.7 | | 2005/0089505 A1 | 4/2005 | Collin |
| 6,726,917 B2 | 4/2004 | Kanji et al. | | 2005/0089541 A1 | 4/2005 | Lacoutiere |
| 6,761,881 B2 | 7/2004 | Bara | | 2005/0118122 A1 | 6/2005 | Simon et al. |
| 6,830,610 B1 | 12/2004 | Bruchert et al. | | 2005/0191327 A1 | 9/2005 | Yu et al. |
| 6,835,399 B2 | 12/2004 | Collin | | 2006/0257336 A1 | 11/2006 | Ferrari et al. |
| 6,852,326 B2 | 2/2005 | Breton | | | | |
| 6,869,594 B2 | 3/2005 | Ferrari | | | FOREIGN PATENT DOCUMENTS | |
| 6,875,245 B2 | 4/2005 | Pavlin | | | | |
| 6,881,400 B2 | 4/2005 | Collin | | CA | 1319306 | 6/1993 |
| 6,960,339 B1 | 11/2005 | Ferrari | | DE | 38 39 136 A1 | 5/1990 |
| 6,979,469 B2 | 12/2005 | Ferrari et al. | | DE | 38 43 892 A1 | 6/1990 |
| 7,008,619 B2 | 3/2006 | Kanji | | DE | 42 08 297 A1 | 9/1993 |
| 7,008,629 B2 | 3/2006 | Kanji | | DE | 42 34 886 A1 | 4/1994 |
| 7,011,523 B2 | 3/2006 | Allred et al. | | DE | 195 43 988 A1 | 5/1997 |
| 7,011,823 B2 | 3/2006 | Ferrari et al. | | DE | 197 07 309 A1 | 8/1998 |
| 7,023,552 B2 | 4/2006 | Simon et al. | | DE | 197 26 184 A1 | 12/1998 |
| 7,025,953 B2 | 4/2006 | Blin et al. | | DE | 197 50 246 A1 | 5/1999 |

| | | | | | | |
|---|---|---|---|---|---|---|
| DE | 197 55 649 | A1 | 6/1999 | EP | 1 095 959 A2 | 5/2001 |
| DE | 198 55 649 | A1 | 6/2000 | EP | 1 114 636 | 7/2001 |
| DE | 199 51 010 | A1 | 4/2001 | EP | 1 114 636 A1 | 7/2001 |
| EP | 0 169 997 | B1 | 2/1986 | EP | 1 213 011 A1 | 6/2002 |
| EP | 0 295 886 | B1 | 12/1988 | EP | 1 213 316 A2 | 6/2002 |
| EP | 0 370 470 | B1 | 5/1990 | EP | 1 343 459 | 1/2007 |
| EP | 0 374 332 | A1 | 6/1990 | EP | 1 359 886 | 3/2007 |
| EP | 0 412 710 | B1 | 2/1991 | FR | 1 529 329 | 5/1968 |
| EP | 0 444 633 | A2 | 9/1991 | FR | 2 232 303 | 1/1975 |
| EP | 0 462 709 | A2 | 12/1991 | FR | 2 315 991 | 1/1977 |
| EP | 0 507 692 | A1 | 10/1992 | FR | 2 416 008 | 8/1979 |
| EP | 0 517 104 | B1 | 12/1992 | FR | 2 528 699 | 6/1983 |
| EP | 0 518 772 | A1 | 12/1992 | FR | 2 674 126 | 9/1992 |
| EP | 0 518 773 | A1 | 12/1992 | FR | 2 785 179 | 5/2000 |
| EP | 0 557 196 | A1 | 8/1993 | FR | 2 791 558 | 10/2000 |
| EP | 0 570 838 | B1 | 11/1993 | FR | 2 796 270 | 1/2001 |
| EP | 0 600 445 | A2 | 6/1994 | FR | 2 796 271 | 1/2001 |
| EP | 0 602 905 | B1 | 6/1994 | FR | 2 796 272 | 1/2001 |
| EP | 0 609 132 | B1 | 8/1994 | FR | 2 796 273 | 1/2001 |
| EP | 0 623 670 | A2 | 11/1994 | FR | 2 796 276 | 1/2001 |
| EP | 0 628 582 | B1 | 12/1994 | FR | 2 796 550 | 1/2001 |
| EP | 0 669 323 | A1 | 8/1995 | FR | 2 802 806 | 6/2001 |
| EP | 0 673 642 | B1 | 9/1995 | FR | 2 804 014 | 7/2001 |
| EP | 0 708 114 | A1 | 4/1996 | FR | 2 804 017 | 7/2001 |
| EP | 0 749 746 | A1 | 12/1996 | FR | 2 804 018 | 7/2001 |
| EP | 0 749 747 | A1 | 12/1996 | FR | 2 804 286 | 8/2001 |
| EP | 0 749 748 | A1 | 12/1996 | FR | 2 810 562 | 12/2001 |
| EP | 0 775 483 | A1 | 5/1997 | FR | 2 811 225 | 1/2002 |
| EP | 0 775 698 | A1 | 5/1997 | FR | 2 811 552 | 1/2002 |
| EP | 0 790 243 | A1 | 8/1997 | FR | 2 816 506 | 5/2002 |
| EP | 0 796 851 | A1 | 9/1997 | FR | 2 817 739 | 6/2002 |
| EP | 0 797 976 | A2 | 10/1997 | FR | 2 817 740 | 6/2002 |
| EP | 0 820 764 | A1 | 1/1998 | FR | 2 817 742 | 6/2002 |
| EP | 0 847 752 | A1 | 6/1998 | FR | 2 817 743 | 6/2002 |
| EP | 0 863 145 | A2 | 9/1998 | FR | 2 819 399 | 7/2002 |
| EP | 0 877 063 | B1 | 11/1998 | FR | 2 819 400 | 7/2002 |
| EP | 0 878 469 | A1 | 11/1998 | FR | 2 819 402 | 7/2002 |
| EP | 0 879 592 | A2 | 11/1998 | GB | 1 117 129 | 6/1968 |
| EP | 0 887 073 | A1 | 12/1998 | GB | 1 194 901 | 6/1970 |
| EP | 0 893 119 | B1 | 1/1999 | GB | 1 194 902 | 6/1970 |
| EP | 0 923 928 | A1 | 6/1999 | GB | 1 220 069 | 1/1971 |
| EP | 0 925 780 | A1 | 6/1999 | GB | 1 273 004 | 5/1972 |
| EP | 0 928 608 | A2 | 7/1999 | GB | 1 444 204 | 7/1976 |
| EP | 0 930 058 | B1 | 7/1999 | GB | 1 539 625 | 1/1979 |
| EP | 0 930 060 | A1 | 7/1999 | GB | 2 014 852 A | 9/1979 |
| EP | 0 933 376 | A2 | 8/1999 | GB | 2 021 411 A | 12/1979 |
| EP | 0 943 340 | A1 | 9/1999 | GB | 2 147 305 A | 5/1985 |
| EP | 0 958 804 | A2 | 11/1999 | GB | 2 196 978 A | 5/1988 |
| EP | 0 958 805 | A2 | 11/1999 | JP | 45-41318 | 12/1970 |
| EP | 0 958 811 | A1 | 11/1999 | JP | 48-38861 | 6/1973 |
| EP | 0 959 066 | A2 | 11/1999 | JP | 49-75740 | 7/1974 |
| EP | 0 959 091 | A1 | 11/1999 | JP | 50/58242 | 5/1975 |
| EP | 0 967 200 | A1 | 12/1999 | JP | 52-007067 | 1/1977 |
| EP | 0 976 390 | A1 | 2/2000 | JP | 53/043577 | 4/1978 |
| EP | 0 984 025 | A2 | 3/2000 | JP | 56/123909 | 9/1981 |
| EP | 1 002 514 | A1 | 5/2000 | JP | 56/166276 | 12/1981 |
| EP | 1 018 332 | | 7/2000 | JP | 61/065809 | 4/1986 |
| EP | 1 031 342 | A1 | 8/2000 | JP | 62/061911 | 3/1987 |
| EP | 1 044 676 | A2 | 10/2000 | JP | 64-90110 | 4/1989 |
| EP | 1 048 282 | A1 | 11/2000 | JP | 2/127568 | 5/1990 |
| EP | 1 053 742 | A1 | 11/2000 | JP | 02/200612 | 8/1990 |
| EP | 1 062 944 | A1 | 12/2000 | JP | 02/207014 | 8/1990 |
| EP | 1 062 959 | A1 | 12/2000 | JP | 2/216279 | 8/1990 |
| EP | 1 064 919 | A1 | 1/2001 | JP | 3/014683 | 1/1991 |
| EP | 1 064 920 | A1 | 1/2001 | JP | 04/346909 | 12/1992 |
| EP | 1 066 814 | A1 | 1/2001 | JP | 5-17710 | 1/1993 |
| EP | 1 068 854 | A1 | 1/2001 | JP | 7/179795 | 7/1995 |
| EP | 1 068 855 | | 1/2001 | JP | 7-258460 | 10/1995 |
| EP | 1 068 855 | A1 | 1/2001 | JP | 7/267827 | 10/1995 |
| EP | 1 068 856 | | 1/2001 | JP | 8/225316 | 9/1996 |
| EP | 1 068 856 | A1 | 1/2001 | JP | 9/20631 | 1/1997 |
| EP | 1 086 945 | A1 | 3/2001 | JP | 9-188830 | 7/1997 |
| EP | 1 090 627 | B1 | 4/2001 | JP | 09/255560 | 9/1997 |

| | | |
|---|---|---|
| JP | 09/263516 | 10/1997 |
| JP | 9/295922 | 11/1997 |
| JP | 10/001444 | 1/1998 |
| JP | 10/007527 | 1/1998 |
| JP | 10/120903 | 5/1998 |
| JP | 10-158450 | 6/1998 |
| JP | 10-158451 | 6/1998 |
| JP | 10-175816 | 6/1998 |
| JP | 10-506643 | 6/1998 |
| JP | 10/212213 | 8/1998 |
| JP | 10/259344 | 9/1998 |
| JP | 11/106216 | 4/1999 |
| JP | 11/335228 | 12/1999 |
| JP | 11/335242 | 12/1999 |
| JP | 11/335254 | 12/1999 |
| JP | 2000038314 A | 2/2000 |
| JP | 2000038316 A | 2/2000 |
| JP | 2000038317 A | 2/2000 |
| JP | 2000038321 A | 2/2000 |
| JP | 2000/503305 | 3/2000 |
| JP | 2000086427 A | 3/2000 |
| JP | 2000086429 A | 3/2000 |
| JP | 2000086438 A | 3/2000 |
| JP | 2000/0154112 | 6/2000 |
| JP | 2001-011340 | 1/2001 |
| JP | 2001-502742 | 2/2001 |
| JP | 2001-081320 | 3/2001 |
| JP | 2001-206821 | 7/2001 |
| JP | 2002/539220 | 11/2002 |
| JP | 2002-539220 | 11/2002 |
| JP | 2004-517906 | 6/2004 |
| WO | WO 86/04916 | 8/1986 |
| WO | WO 87/03783 | 7/1987 |
| WO | WO 91/12793 | 9/1991 |
| WO | WO 93/04665 | 3/1993 |
| WO | WO 93/21763 | 11/1993 |
| WO | WO 93/23008 | 11/1993 |
| WO | WO 94/18261 | 8/1994 |
| WO | WO 94/21233 | 9/1994 |
| WO | WO 95/15741 | 6/1995 |
| WO | WO 95/24887 | 9/1995 |
| WO | WO 95/33000 | 12/1995 |
| WO | WO 96/15761 | 5/1996 |
| WO | WO 96/38126 | 5/1996 |
| WO | WO 96/40044 | 12/1996 |
| WO | WO 97/17057 | 5/1997 |
| WO | WO 97/36573 | 10/1997 |
| WO | WO 98/17243 | 4/1998 |
| WO | WO 98/17705 | 4/1998 |
| WO | WO 98/22078 | 5/1998 |
| WO | WO 98/25922 | 6/1998 |
| WO | WO 98/27162 | 6/1998 |
| WO | WO 98/42298 | 10/1998 |
| WO | WO 98/47470 | 10/1998 |
| WO | WO 98/52534 | 11/1998 |
| WO | WO 98/58623 | 12/1998 |
| WO | WO 99/24002 | 5/1999 |
| WO | WO 99/36477 | 7/1999 |
| WO | WO 99/43297 | 9/1999 |
| WO | WO 99/66888 | 12/1999 |
| WO | WO 00/06114 | 2/2000 |
| WO | WO 00/27350 | 5/2000 |
| WO | WO 00/40216 | 7/2000 |
| WO | WO 00/61080 | 10/2000 |
| WO | WO 00/61081 | 10/2000 |
| WO | WO 00/74519 A2 | 12/2000 |
| WO | WO 01/51020 A1 | 7/2001 |
| WO | WO 01/52799 A1 | 7/2001 |
| WO | WO 95/24887 A | 9/2001 |
| WO | WO 01/97758 A2 | 12/2001 |
| WO | WO 01/97773 A1 | 12/2001 |
| WO | WO 02/03932 A2 | 1/2002 |
| WO | WO 02/03935 A2 | 1/2002 |
| WO | WO 02/03950 A2 | 1/2002 |
| WO | WO 02/03951 A2 | 1/2002 |
| WO | WO 02/47605 A2 | 6/2002 |
| WO | WO 02/47606 A2 | 6/2002 |
| WO | WO 02/47608 A2 | 6/2002 |
| WO | WO 02/47619 A2 | 6/2002 |
| WO | WO 02/47620 A2 | 6/2002 |
| WO | WO 02/47622 A2 | 6/2002 |
| WO | WO 02/47627 A1 | 6/2002 |
| WO | WO 02/47629 A1 | 6/2002 |
| WO | WO 02/47630 A1 | 6/2002 |
| WO | WO 02/47658 A2 | 6/2002 |
| WO | WO 02/49583 A1 | 6/2002 |
| WO | WO 02/49601 A1 | 6/2002 |
| WO | WO 02/055030 A2 | 7/2002 |
| WO | WO 02/055031 A1 | 7/2002 |
| WO | WO 02/056845 A1 | 7/2002 |
| WO | WO 02/056847 A1 | 7/2002 |
| WO | WO 02/056848 A1 | 7/2002 |
| WO | WO 02/058642 | 8/2002 |
| WO | WO 02/092047 A1 | 11/2002 |
| WO | WO 02/092663 A1 | 11/2002 |
| WO | WO 02/102322 A2 | 12/2002 |
| WO | WO 05/013887 A2 | 2/2005 |

OTHER PUBLICATIONS

Certified English translation of FR 1 529 329.
Charles M. Hansen, "The Three Dimensional Solubility Parameter—Key to Paint Component Affinities: I. Solvents, Plasticizers, Polymers, and Resins," Journal of Paint Technology, vol. 39, No. 505, Feb. 1967, pp. 104-117.
English language abstract of JP 53/043577 from Patent Abstracts of Japan.
English language abstract of JP 56/123909 from Patent Abstracts of Japan.
English language abstract of JP 56/166276 from Patent Abstracts of Japan.
English language abstract of JP 78/043577.
English language DERWENT abstract of DE 195 43 988 A1.
English language DERWENT abstract of DE 197 07 309 A1.
English language DERWENT abstract of DE 197 50 246 A1.
English language DERWENT abstract of DE 199 51 010 A1.
English language DERWENT abstract of DE 38 39 136 A1.
English language DERWENT abstract of DE 38 43 892 A1.
English language DERWENT abstract of DE 42 08 297 A1.
English language DERWENT abstract of DE 42 34 886 A1.
English language DERWENT abstract of EP 0 169 997 B.
English language DERWENT abstract of EP 0 557 196 A1.
English language DERWENT abstract of EP 0 609 132 B1.
English language DERWENT abstract of EP 0 749 746 A1.
English language DERWENT abstract of EP 0 749 747 A1.
English language DERWENT abstract of EP 0 749 748 A1.
English language DERWENT abstract of EP 0 775 483 A1.
English language DERWEBT abstract of EP 0 820 764 A1.
English language DERWENT abstract of EP 0 847 752 A1.
English language DERWENT abstract of EP 0 879 592 A2.
English language DERWENT abstract of EP 0 887 073 A1.
English language DERWENT abstract of EP 0 923 928 A1.
English language DERWENT abstract of EP 0 925 780 A1.
English language DERWENT abstract of EP 0 930 058 B1.
English language DERWENT abstract of EP 0 930 060 A1.
English language DERWENT abstract of EP 0 943 340 A1.
English language DERWENT abstract of EP 0 958 811 A1.
English language DERWENT abstract of EP 0 959 066 A2.
English language DERWENT abstract of EP 0 959 091 A1.
English language DERWENT abstract of EP 0 976 390 A1.
English language DERWENT abstract of EP 1 002 514 A1.
English language DERWENT abstract of EP 1 031 342 A1.
English language DERWENT abstract of EP 1 048 282 A1.
English language DERWENT abstract of EP 1 053 742 A1.
English language DERWENT abstract of EP 1 064 919 A1.
English language DERWENT abstract of EP 1 064 920 A1.

English language DERWENT abstract of EP 1 066 814 a1.
English language DERWENT abstract of EP 1 068 854 A1.
English language DERWENT abstract of EP 1 068 855 A1.
English language DERWENT abstract of EP 1 068 856 A1.
English language DERWENT abstract of EP 1 086 945 A1.
English language DERWENT abstract of EP 1 090 627 B1.
English language DERWENT abstract of EP 1 114 636 A1.
English language DERWENT abstract of FR 2 232 303.
English language DERWENT abstract of FR 2 674 126.
English language DERWENT abstract of FR 2 785 179.
English language DERWENT abstract of FR 2 796 270.
English language DERWENT abstract of FR 2 796 271.
English language DERWENT abstract of FR 2 796 272.
English language DERWENT abstract of FR 2 796 273.
English language DERWENT abstract of FR 2 796 276.
English language DERWENT abstract of FR 2 802 806.
English language DERWENT abstract of FR 2 804 017.
English language DERWENT abstract of FR 2 804 018.
English language DERWENT abstract of FR 2 810 562.
English language DERWENT abstract of FR 2 811 225.
English language DERWENT abstract of FR 2 811 552.
English language DERWENT abstract of FR 2 816 506.
English language DERWENT abstract of FR 2 817 739.
English language DERWENT abstract of FR 2 817 740.
English language DERWENT abstract of FR 2 817 743.
English language DERWENT abstract of FR 2 819 399.
English language DERWENT abstract of FR 2 819 400.
English language DERWENT abstract of FR 2 819 402.
English language DERWENT abstract of JP 02/200612.
English language DERWENT abstract of JP 04/346909.
English language DERWENT abstract of JP 09/255560.
English language DERWENT abstract of JP 10/007527.
English language DERWENT abstract of JP 10/120903.
English language DERWENT abstract of JP 10/212213.
English language DERWENT abstract of JP 10/259344.
English language DERWENT abstract of JP 11/106216.
English language DERWENT abstract of JP 11/335228.
English language DERWENT abstract of JP 11/335242.
English language DERWENT abstract of JP 11/335254.
English language DERWENT abstract of JP 2/127568.
English language DERWENT abstract of JP 2000038314 A.
English language DERWENT abstract of JP 2000038316 A and JP 2000038317 A.
English language DERWENT abstract of JP 2000038321 A.
English language DERWENT abstract of JP 2000086427 A.
English language DERWENT abstract of JP 2000086429 A.
English language DERWENT abstract of JP 2000086438 A.
English language DERWENT abstract of JP 2216279.
English language DERWENT abstract of JP 3014683.
English language DERWENT abstract of JP 61065809.
English language DERWENT abstract of JP 62061911.
English language DERWENT abstract of JP 7179795.
English language DERWENT abstract of JP 7267827.
English language DERWENT abstract of JP 8225316.
English language DERWENT abstract of JP 920631.
English language DERWENT abstract of JP 9295922.
English language DERWENT abstract of WO 01/97773.
English language DERWENT abstract of WO 02/056847.
English language DERWENT abstract of WO 02/056848.
English language DERWENT abstract of WO 02/47622.
English language DERWENT abstract of WO 02/47629.
English language DERWENT abstract of WO 02/47630.
English language DERWENT abstract of WO 86/04916.
Estee Lauder MagnaScopic Maximum Volume mascara product packaging, believed to have first been sold in 2003.
Estee Lauder's Response to Plaintiff's First Set of Interrogatories (Nos. 1-6), dated Sep. 27, 2004, in the on-going litigation *L'Oreal S.A., et al.* v. *The Estee Lauder Companies Inc., et al.*, Civil Action No. 04-1660 (D.N.J.).
French Search Report in FR 0000920 (priority document for PCT/FR01/00229, which is the priority document), dated Nov. 10, 2000.
French Search Report in FR 0001004, dated Nov. 10, 2000.
French Search Report in FR 0008084, dated Mar. 28, 2001.
French Search Report in FR 0008913, dated Mar. 20, 2001.
French Search Report in FR 0016161, dated Sep. 6, 2001.
French Search Report in FR 0016163, dated Aug. 1, 2001.
French Search Report in FR 0016164, dated Sep. 6, 2001.
French Search Report in FR 0016180, dated Oct. 16, 2001.
French Search Report in FR 0100479, dated Sep. 17, 2001.
French Search Report in FR 0100620, dated Nov. 6, 2001.
French Search Report in FR 0100623, dated Oct. 9, 2001.
French Search Report in FR 0114529, dated Aug. 26, 2002.
French Search Report in FR 0114530, dated Aug. 26, 2002.
French Search Report in FR 9909176, dated Mar. 23, 2000.
French Search Report in FR 9909177, dated Mar. 30, 2000.
French Search Report in FR 9916588, dated Oct. 16, 2000.
Handbook of Cosmetic Science and Tech. Elsevier Advanced Tech., 1st Edition (1994), pp. 1-32.
International Search Report in PCT/FR01/00229, dated Apr. 18, 2001.
International Search Report in PCT/FR01/01958, dated Oct. 26, 2001.
International Search Report in PCT/FR01/03726, dated Apr. 18, 2002.
International Search Report in PCT/FR01/03937, dated Apr. 23, 2002.
International Search Report in PCT/FR01/03938, dated Jun. 10, 2002.
International Search Report in PCT/FR01/03939 (priority document for FR 0016164), dated Apr. 15, 2002.
International Search Report in PCT/FR01/03940 (priority document for FR 0016161), dated Mar. 13, 2002.
International Search Report in PCT/FR01/03945 (priority document for FR 0016163), dated May 31, 2002.
International Search Report in PCT/FR02/00129, dated Jun. 14, 2002.
International Search Report in PCT/FR02/00144 (priority document for FR 0100479), dated Jun. 14, 2002.
International Search Report in PCT/FR02/00194, dated Jun. 12, 2002.
International Search Report in PCT/IB00/02000, dated Aug. 8, 2001.
International Search Report in PCT/IB00/02002, dated Sep. 4, 2001.
International Search Report in PCT/IB00/02006, dated Aug. 8, 2001.
International Search Report in PCT/IB01/02780, dated Oct. 4, 2002.
International Search Report in PCT/IB01/02786, dated Oct. 2, 2002.
International Search Report in PCT/IB01/02820, dated May 27, 2002.
International Search Report in PCT/IB01/02833, dated May 24, 2002.
International Search Report in PCT/IB01/02840, dated Jun. 11, 2002.
International Search Report in PCT/US 00/33596, dated Aug. 8, 2001.
International Search Report in PCT/US 01/47454, dated Aug. 29, 2002.
International Search Report in PCT/US 01/47459, dated Feb. 6, 2003.
International Search Report in PCT/US 01/47496, dated Feb. 26, 2003.
International Search Report in PCT/US 01/47497, dated Dec. 2, 2002.
International Search Report in PCT/US 01/47499, dated Aug. 8, 2002.
Kenji Hanabusa et al., Easy Preparation and Prominent Gelation of New Gelator Based on L-Lysine, 2000 Chem. Letters, 1070-1071.
Kenji Hanabusa et al., Prominent Gelation and Chiral Aggregation of Alkylamides Derived from trans-1,2-Diaminocyclohexane, Angew. Chem. Int. Ed. Engl. 1996, 35, No. 17, 1949-1951.
Kenji Hanabusa et al., Terephthaloyl Derivatives as New Gelators; Excellent Gelation Ability and Remarkable Increase of Gel Strength by Adding Polymers, 1999 Chemistry Letters 767-768.
Kirk-Othmer, "Encyclopedia of Chemical Technology", Third Edition, vol. 22, John Wiley & Sons, 1983, pp. 332-342.
McCutcheon's vol. 1: Emulsifiers & Detergents, North American Edition MC Publishing Co., Glen Rock NJ (1993), pp. 272-273.
Milan Jokic et al., A Novel Type of Small Organic Gelators: Bis(Amino Acid) Oxalyl Amides, 1995 J. Chem. Soc., Chem. Commun., 1723-1724.

Origins Full Story™ Lush lash mascara product packaging, believed to have first been sold in 2003.

P. Terech, "Low-Molecular Weight Organogelators," in Specialist Surfactants, ch. 8, pp. 208-268 (I.D. Robb, ed., 1997).

Partial International Search Report in PCT/US 01/47497, dated Nov. 15, 2002.

Toshimi Shimizu et al., Stereochemical Effect of Even-Odd Connecting Links on Supramolecular Assemblies Made of 1-Glucosamide Bolaamphiphiles, J. Am. Chem. Soc. 1997, 119, 2812-2818.

U.S. District Court for the District of New Jersey Civil Docket for L'Oreal S.A. et al. v. Estee Lauder Companies, Inc., et al., Civ. No. 04-1660 (HAA) (filed Apr. 4, 2004) (retrieved Jan. 2, 2005).

Xuzhong Luo et al., Self-assembled organogels formed by monoalkyl derivatives of oxamide, 2000 Chem. Commun. 2091-92.

Yasuda et al., Novel Low-molecular-weight Organic Gels: N,N', N''-Tristearyltrimesamide/Organic Solvent System, Chemistry Letters, pp. 575-576, 1996, the month of publication is not available.

English language DERWENT Abstract for FR 2 528 699.

English language DERWENT Abstract for JP 10-158450.

English language DERWENT Abstract for JP 10-158451.

English language DERWENT Abstract for JP 10/506643.

English language DERWENT Abstract for JP 2001-011340.

English language DERWENT Abstract for JP 5-17710.

English language DERWENT Abstract for JP 7-258460.

English language DERWENT Abstract for JP 9-188830.

Estee Lauder's Amended Answer and Counterclaims, dated Apr. 21, 2005, in the on-going litigation L'Oreal S.A., et al., v. The Estee Lauder Companies Inc., et al., Civil Action No. 04-1660 (D.N.J.).

Estee Lauder's Answer and Counterclaims, dated May 27, 2004, in the on-going litigation L'Oreal S.A., et al., v. The Estee Lauder Companies Inc., et al., Civil Action No. 04-1660 (D.N.J.).

Estee Lauder's Response to Plaintiff's Third Set of Interrogatories (Nos. 8-13), dated Jun. 21, 2005, in the on-going litigation L'Oreal S.A., et al. v. The Estee Lauder Companies Inc., et al., Civil Action No. 04-1660 (D.N.J.).

L'Oreal's Complaint for Patent Infringement, dated Apr. 7, 2004, in the on-going litigation L'Oreal S.A., et al., v. The Estee Lauder Companies Inc., et al., Civil Action No. 04-1660 (D.N.J.).

Office Action in co-pending U.S. Appl. No. 09/733,896 dated Jul. 13, 2005.

Office Action in co-pending U.S. Appl. No. 09/733,897 dated Jul. 27, 2006.

Office Action in co-pending U.S. Appl. No. 09/733,898 dated Apr. 25, 2005.

Office Action in co-pending U.S. Appl. No. 09/733,899 dated May 3, 2005.

Office Action in co-pending U.S. Appl. No. 09/733,900, dated Jun. 2, 2005.

Office Action in co-pending U.S. Appl. No. 09/749,036 dated Apr. 29, 2005.

Office Action in co-pending U.S. Appl. No. 10/012,052, dated Jun. 3, 2005.

Office Action in co-pending U.S. Appl. No. 10/012,052, dated Nov. 17, 2006.

Office Action in co-pending U.S. Appl. No. 10/129,377 dated Oct. 10, 2006.

Office Action in co-pending U.S. Appl. No. 10/203,254 dated Apr. 22, 2005.

Office Action in co-pending U.S. Appl No. 10/203,375, dated May 13, 2005.

Office Action in co-pending U.S. Appl. No. 10/312,083 dated Apr. 18, 2005.

Office Action in co-pending U.S. Appl. No. 10/312,083 dated Sep. 25, 2006.

Office Action in co-pending U.S. Appl. No. 10/459,636, dated Aug. 31, 2006.

Office Action in co-pending U.S. Appl. No. 10/699,780, dated Jun. 15, 2005.

Office Action in co-pending U.S. Appl. No. 10/699,780, dated Sep. 25, 2006.

Office Action in co-pending U.S. Appl. No. 10/746,612 dated Nov. 3, 2006.

Office Action in co-pending U.S. Appl. No. 11/212,811 dated Aug. 24, 2006.

Richard J. Lewis, Sr., "Ricinoleic Acid," Hawley's Condensed Chemical Dictionary 972 (13th. 1997).

Bangham, A.D. et al. Diffusion of Univalent Ions across the Lamellae of Swollen Phospholipids, Journal of Molecular Biology, pp. 238-252, vol. 13, Aug. to Oct. 1965.

Co-Pending U.S. Appl. No. 10/494,864; Title: Composition Containing an Amino Acid N-acylated Ester and a Polyamide-Structured UV Filter filed Nov. 23, 2004.

Co-Pending U.S. Appl. No. 11/212,811, Title: A Transfer-Free Mascara Composition Comprising At Least One Volatile Solvent and At Least One Polymer filed Aug. 29, 2005.

Co-Pending U.S. Appl. No. 11/312,338, Title: Composition and Process for Coating Keratin filed Dec. 21, 2005.

Co-Pending U.S. Appl. No. 11/351,309, Title: Cosmetic Composition Containing a Polymer and a Fluoro Oil filed Feb. 10, 2006.

Co-Pending U.S. Appl. No. 11/406,371; Title: Cosmetic Composition Comprising Silica Particles, Reflecting Particles, and At Least One Polymer, Preparative Process, and Uses Thereof filed Apr. 19, 2006.

English language Abstract from Patent Abstracts of Japan for JP 2000/0154112.

English Language Abstract of FR 2 804 014 from esp@cenet.

English Language Abstract of FR 2 817 742 from esp@cenet.

English language abstract of JP 02/207014 from Patent Abstracts of Japan.

English language Derwent abstract for JP 09/263516.

English language Derwent abstract for JP 45-41318.

English language Derwent abstract for JP 48-38861.

English language Derwent abstract for JP 49-75740.

English language Derwent abstract for JP 64-90110.

English language DERWENT abstract of DE 197 26 184.

English language DERWENT abstract of DE 197 55 649 A1.

English language DERWENT abstract of DE 198 55 649 A1.

English language DERWENT abstract of EP 0 507 692 A1.

English language DERWENT abstract of EP 0 518 772 A1.

English language DERWENT abstract of EP 0 518 773 A1.

English language DERWENT abstract of EP 0 669 323 A1.

English language DERWENT abstract of EP 0 775 698 A1.

English language DERWENT abstract of EP 0 790 243 A1.

English language DERWENT abstract of EP 0 863 145 A2.

English language DERWENT abstract of EP 0 878 469 A1.

English language DERWENT abstract of EP 0 967 200 A1.

English language DERWENT abstract of FR 2 315 991.

English language DERWENT abstract of FR 2 416 008.

English language DERWENT abstract of FR 2 796 550.

English language DERWENT abstract of FR 2 804 286.

English language DERWENT abstract of WO 93/04665.

English language DERWENT abstract of WO 98/25922.

English language esp@cenet abstract for JP 10/001444.

English language esp@cenet abstract for JP 52/007067.

Harry's Cosmeticology 375-383 (J.B. Wilkinson & R.J. Moore eds., Chemical Pub. 7th ed. 1982).

International Search Report in PCT/US03/41618, dated Mar. 11, 2005.

International Search Report in PCT/US04/01071, dated Feb. 22, 2005.

Office Action in co-pending U.S. Appl. No. 09/733,896 dated Jan. 30, 2006.

Office Action in co-pending U.S. Appl. No. 09/733,897 dated Feb. 8, 2006.

Office Action in co-pending U.S. Appl. No. 09/733,898 dated Jan. 11, 2006.

Office Action in co-pending U.S. Appl. No. 09/749,036 dated Nov. 23, 2005.

Office Action in co-pending U.S. Appl. No. 10/129,377 dated Jan. 13, 2006.

Office Action in co-pending U.S. Appl. No. 10/182,830 dated Apr. 4, 2005.

Office Action in co-pending U.S. Appl. No. 10/182,830 dated Nov. 25, 2005.

Office Action in co-pending U.S. Appl. No. 10/182,830, dated May 17, 2006.
Office Action in co-pending U.S. Appl. No. 10/203,254 dated Dec. 5, 2005.
Office Action in co-pending U.S. Appl. No. 10/203,254 dated Jun. 1, 2006.
Office Action in co-pending U.S. Appl. No. 10/312,083 dated Sep. 28, 2005.
Office Action in co-pending U.S. Appl. No. 10/312,083 dated Apr. 6, 2006.
Office Action in co-pending U.S. Appl. No. 10/746,612 dated Feb. 17, 2006.
Office Action in co-pending U.S. Appl. No. 10/746,612 dated Jun. 15, 2005.
Office Action in co-pending U.S. Appl. No. 10/787,441, datd Apr. 5, 2005.
Office Action in co-pending U.S. Appl. No. 10/990,475 dated May 1, 2006.
Office Action in co-pending U.S. Appl. No. 10/990,475 dated Nov. 2, 2005.
Office Action in co-pending U.S. Appl. No. 11/212,811 dated Nov. 17, 2005.
Richard J. Lewis, Sr., "Fatty Acid," Hawley's Condensed Chemical Dictionary 487 (13th ed., 1997).
English Language Abstract of JP1090110 from esp@cenet.
English Language Abstract of JP52007067 from esp@cenet.
English Language Abstract of WO 0055264 from esp@cenet.
English Language Abstract of JP10001444 from esp@cenet.
English language DERWENT abstract for EP 1 382 322 A2.
English language esp@cenet abstract for EP 1 477 154 A1.
English language esp@cenet abstract for FR 2 659 011 A1.
English language esp@cenet abstract for FR 2 848 822 A1.
English language esp@cenet abstract for JP 04-230312.
English language esp@cenet abstract for JP 06-299075.
English language esp@cenet abstract for JP 10-67618.
English language esp@cenet abstract for JP 10-251118.
English language esp@cenet abstract for JP 10-306012.
English Language Abstract for JP 10-120903.
English language esp@cenet abstract for JP 11-236314.
English language DERWENT abstract for JP 2000-063674.
English language Abstract for JP 2003-055155.
English language esp@cenet abstract of JP 7-89826.
English language Abstract for WO 02/47606.
English language Abstract for WO 98/31329.
Irving R. Schmolka. PhD., "Gel Cosmetics," Cosmetics & Toletries, vol. 99, pp. 69-76, Nov. 1984.
Office Action for co-pending U.S. Appl. No. 09/733,900 dated May 1, 2009.
Office Action in co-pending U.S. Appl. No. 09/685,578 dated Jul. 30, 2007.
Office Action in co-pending U.S. Appl. No. 09/685,578 dted Apr. 7, 2008.
Office Action in co-pending U.S. Appl. No. 09/733,897 dated Jan. 18, 2007.
Office Action in co-pending U.S. Appl. No. 09/733,897 dated Jun. 23, 2009.
Office Action in co-pending U.S. Appl. No. 09/733,897 dated Feb. 7, 2008.
Office Action in co-pending U.S. Appl. No. 09/733,899 dated Apr. 27, 2009.
Office Action in co-pending U.S. Appl. No. 09/749,036 dated Aug. 24, 2007.
Office Action in co-pending U.S. Appl. No. 09/749,036 dated Jan. 17, 2007.
Office Action in co-pending U.S. Appl. No. 09/749,036 dated Mar. 6, 2009.
Office Action in co-pending U.S. Appl. No. 10/012,052 dated Mar. 6, 2009.
Office Action in co-pending U.S. Appl. No. 10/129,377 dated Jul. 13, 2007.
Office Action in co-pending U.S. Appl. No. 10/450,108 dated Mar. 21, 2007.
Office Action in co-pending U.S. Appl. No. 10/466,166 dated Apr. 1, 2009.
Office Action in co-pending U.S. Appl. No. 10/466,166 dated Jun. 25, 2007.
Office Action in co-pending U.S. Appl. No. 10/466,166 date Feb. 27, 2008.
Office Action in co-pending U.S. Appl. No. 10/494,864 dated Mar. 6, 2009.
Office Action in co-pending U.S. Appl. No. 10/699,780 dated Oct. 9, 2007.
Office Action in co-pending U.S. Appl. No. 10/746,612 dated Jul. 22, 2009.
Office Action in co-pending U.S. Appl. No. 10/747,412 dated Jun. 10, 2009.
Office Action in co-pending U.S. Appl. No. 10/918,579 dated May 21, 2008.
Office Action in co-pending U.S. Appl. No. 10/918,579, dated Jan. 25, 2008.
Office Action in co-pending U.S. Appl. No. 10/990,475 dated Jan. 23, 2007.
Office Action in co-pending U.S. Appl. No. 10/993,431 dated Oct. 18, 2007.
Office Action in co-pending U.S. Appl. No. 11/212,811 dated Mar. 21, 2008.
Office Action in co-pending U.S. Appl. No. 11/212,811 dated May 17, 2007.
Re-exam Control No. 90/010,002, Title: Stable Cosmetic Emulsion with Polyamide Gelling Agent: Third Party Reply Under 37 C.F.R. 1.535 After Patent Owner's Statement, filed Jan. 8, 2008.
Re-exam Control No. 90/012,002, Response Pursuant to 37 C.F.R. 1.530(b), Patent Owner's Statement, filed Nov. 20, 2007.
Re-exam Control No. 90/012,002; Title: Stable Cosmetic Emulsion With Polyamide Gelling Agent Request for Reexamination filed Jul. 18, 2007.
Richard H. Lewis, Sr., "Fatty Acid," Hawley's Condensed Chemical Dictionary 487 (13th ed., 1997).

\* cited by examiner

COSMETIC COMPOSITIONS COMPRISING A STRUCTURING AGENT, SILICONE POWDER AND SWELLING AGENT

RELATED APPLICATIONS

This application is a continuation of U.S. patent application Ser. No. 10/618,315, filed Jul. 11, 2003, now abandoned, which is incorporated by reference.

BACKGROUND OF THE INVENTION

Many cosmetic compositions, including pigmented cosmetics such as foundations, concealers, lipsticks, mascaras, and other cosmetic and sunscreen compositions, have been developed for comfortable application and wear. However many of these compositions are difficult to apply and do not have a smooth feel upon application. Furthermore, compositions may have a tendency to be tacky, resulting in poor application and spreadability characteristics.

There is still a need, therefore, for improved longwearing cosmetic compositions with cushiony, soft and silky feel upon application.

SUMMARY OF THE INVENTION

One aspect of the present invention is directed to a cosmetic composition, comprising: a structuring agent comprising a polymer skeleton having a hydrocarbon-based repeating unit comprising at least one hetero atom; a liquid fatty phase; a silicone elastomer powder comprising a silicone elastomer core coated with a silicone resin; and a swelling agent for said powder.

Another aspect of the present invention is directed to a composition useful in the preparation of a cosmetic, comprising: a structuring agent comprising a polymer skeleton comprising a hydrocarbon-based repeating unit containing at least one hetero atom, and a silicone elastomer powder comprising a silicone elastomer core coated with a silicone resin. Methods of making the compositions covered by these aspects of the present invention are also provided.

A further aspect of the present invention is directed to a method for care, make-up or treatment of a keratin material, comprising applying to the keratin material a composition comprising a structuring agent comprising a polymer skeleton having a hydrocarbon-based repeating unit comprising at least one hetero atom; a liquid fatty phase; a silicone elastomer powder comprising a silicone elastomer core coated with a silicone resin; and a swelling agent for the powder.

In preferred embodiments of each of these aspects of the present invention, the structural agent comprises a polyamide bonded to a fatty chain via an ester group, the swelling agent comprises a dimethicone, and the silicone elastomer core comprises a polyorganosilsesquioxane which may contain pendant functionalized groups such as fluoroalkyl or phenyl groups.

The compositions of the present invention may take a variety of forms of purposes of finished products. For example, the compositions may take any number of forms, including a paste, a gel (e.g., a solid, rigid or supple gel, including an anhydrous gel such as a translucent anhydrous gel or a transparent anhydrous gel), a cream, an emulsion (an aqueous or anhydrous emulsion), a solid (e.g., a molded composition or cast as a stick (e.g., a poured or molded stick), a compact, a dish, or a powder (e.g., a loose, compact or pressed powder). In addition, while compositions of the invention are described in terms of being cosmetic compositions, to the extent that they are intended to be applied to skin, they may also be considered as dermatological compositions, particularly if they contain a drug or other active agent considered to treat or benefit skin.

DETAILED DESCRIPTION OF THE INVENTION

The Structuring Polymer

The at least one structuring agent in the compositions of the present invention are solids that are not deformable at room temperature (25° C.) and atmospheric pressure (760 mmHg). The structuring agent contributes to the overall structure of the composition. In some embodiments, the agent does not make the compositions opaque. As defined above, the at least one structuring polymer of the present invention comprises a polymer skeleton comprising at least one hydrocarbon-based repeating unit comprising at least one hetero atom. In one embodiment, the at least one structuring polymer further comprises at least one terminal fatty chain chosen from alkyl and alkenyl chains, such as of at least 4 atoms, and further such as comprising 8 to 120 carbon atoms, bonded to the polymer skeleton via at least one linking group. The terminal fatty chain may be functionalized. The at least one structuring polymer may also further comprise at least one pendant fatty chain chosen from alkyl and alkenyl chains, such as of at least 4 atoms, and further such as comprising 8 to 120 carbon atoms, bonded to any carbon or hetero atom of the polymer skeleton via at least one linking group. The pendant fatty chain may, for example, be functionalized. The at least one structuring polymer may comprise both at least one pendant fatty chain and at least one terminal fatty chain as defined above, and one or both types of chains can be functionalized.

In one embodiment, the structuring polymer comprises at least two hydrocarbon-based repeating units. As a further example, the structuring polymer comprises at least three hydrocarbon-based repeating units and as an even further example, the at least three repeating units are identical.

As used herein, "functionalized" means comprising at least one functional group. Non-limiting examples of functional groups include hydroxyl groups, ether groups, oxyalkylene groups, polyoxyalkylene groups, carboxylic acid groups, amine groups, amide groups, halogen containing groups, including fluoro and perfluoro groups, halogen atoms, ester groups, siloxane groups and polysiloxane groups.

For purposes of the invention, the expression "functionalized chain" means, for example, an alkyl chain comprising at least one functional (reactive) group chosen, for example, from those recited above. For example, in one embodiment, the hydrogen atoms of at least one alkyl chain may be substituted at least partially with fluorine atoms.

According to the invention, these chains may be linked directly to the polymer skeleton or via an ester function or a perfluoro group.

For the purposes of the invention, the term "polymer" means a compound containing at least 2 repeating units, such as, for example, a compound containing at least 3 repeating units, which may be identical.

As used herein, the expression "hydrocarbon-based repeating unit" includes a repeating unit comprising from 2 to 80 carbon atoms, such as, for example, from 2 to 60 carbon atoms. The at least one hydrocarbon-based repeating unit may also comprise oxygen atoms. The hydrocarbon-based repeating unit may be chosen from saturated and unsaturated hydrocarbon-based repeating units which in turn may be chosen from linear hydrocarbon-based repeating units, branched hydrocarbon-based repeating units and cyclic hydrocarbon-based repeating units. The at least one hydrocarbon-based repeating unit may comprise, for example, at least one hetero atom that is part of the polymer skeleton, i.e., not pendant. The at least one hetero atom may be chosen, for example, from nitrogen, sulphur, and phosphorus. For example, the at least one hetero atom may be a nitrogen atom, such as a non-pendant nitrogen atom. In another embodiment, the at least one hydrocarbon-based repeating unit may comprise at least one hetero atom with the proviso that the at least one hetero atom is not nitrogen. In another embodiment, the at least one hetero atom is combined with at least one atom chosen from oxygen and carbon to form a hetero atom group. In one embodiment, the hetero atom group comprises a carbonyl group.

The at least one repeating unit comprising at least one hetero atom may be chosen, for example, from amide groups, carbamate groups, and urea groups. In one embodiment, the at least one repeating unit comprises amide groups forming a polyamide skeleton. In another embodiment, the at least one repeating unit comprises carbamate groups and/or urea groups forming a polyurethane skeleton, a polyurea skeleton and/or a polyurethane-polyurea skeleton. The pendant chains, for example, can be linked directly to at least one of the hetero atoms of the polymer skeleton. In yet another embodiment, the at least one hydrocarbon-based repeating unit may comprise at least one hetero atom group with the proviso that the at least one hetero atom group is not an amide group. In one embodiment, the polymer skeleton comprises at least one repeating unit chosen from silicone units and oxyalkylene units, the at least one repeating unit being between the hydrocarbon-based repeating units.

In one embodiment, the compositions of the invention comprise at least one structuring polymer with nitrogen atoms, such as amide, urea, or carbamate units, such as amide units, and at least one polar oil.

In one embodiment, in the at least one structuring polymer, the percentage of the total number of fatty chains ranges from 40% to 98% relative to the total number of repeating units and fatty chains, and as a further example, from 50% to 95%. In a further embodiment wherein the polymer skeleton is a polyamide skeleton, in the at least one structuring polymer, the percentage of the total number of fatty chains ranges from 40% to 98% relative to the total number of all amide units and fatty chains, and as a further example, from 50% to 95%.

In a further embodiment, the nature and proportion of the at least one hydrocarbon-based repeating unit comprising at least one hetero atom depend on the nature of a liquid fatty phase of the composition and are, for example, similar to the nature of the fatty phase. For example, not to be limited as to theory, the more polar the hydrocarbon-based repeating units containing a hetero atom, and in high proportion, which corresponds to the presence of several hetero atoms, the greater the affinity of the at least one structuring polymer to polar oils. Conversely, the more non-polar, or even apolar, and lesser in proportion the hydrocarbon-based repeating units containing a hetero atom, the greater the affinity of the polymer for apolar oils. In another embodiment, the invention is drawn to a structured composition containing at least one liquid fatty phase structured with at least one structuring polymer, wherein the at least one structuring polymer is a polyamide comprising a polymer skeleton comprising at least one amide repeating unit and optionally at least one pendant fatty chain and/or at least one terminal chain that are optionally functionalized and comprise from 8 to 120 carbon atoms, bonded to at least one of the amide repeating units via at least one linking group. The liquid fatty phase further contains at least one organogellator for gelling the liquid fatty phase. The at least one liquid fatty phase, the at least one structuring polyamide and the at least one organogellator together form a physiologically acceptable medium.

When the structuring polymer has amide-repeating units, the pendant fatty chains may be linked to at least one of the nitrogen atoms in the amide-repeating units.

The structuring polymer, for example the polyamide polymer, may have a weight-average molecular mass of less than 100,000, such as less than 50,000. In another embodiment, the weight-average molecular mass may range from 1000 to 30,000, such as from 2000 to 20,000, further such as from 2000 to 10,000.

As discussed, the at least one structuring polymer may, for example, be chosen from polyamide polymers. A polyamide polymer may comprise, for example, a polymer skeleton that comprises at least one amide-repeating unit, i.e., a polyamide skeleton. In one embodiment, the polyamide skeleton may further comprise at least one terminal fatty chain chosen from alkyl chains, for example, alkyl chains comprising at least four carbon atoms, and alkenyl chains, for example, alkenyl chains comprising at least four carbon atoms, bonded to the at least one polyamide skeleton via at least one linking group, and/or at least one pendant fatty chain chosen from alkyl chains, for example, alkyl chains comprising at least four carbon atoms, and alkenyl chains, for example, alkenyl chains comprising at least four carbon atoms, bonded to the at least one polyamide skeleton via at least one linking group. In one embodiment, the polyamide skeleton may comprise at least one terminal fatty chain chosen from fatty chains comprising 8 to 120 carbon atoms, such as, for example, 12 to 68 carbon atoms, bonded to the at least one polyamide skeleton via at least one linking group and/or at least one pendant fatty chain chosen from fatty chains comprising 8 to 120 carbon atoms, such as, for example, 12 to 68 carbon atoms, bonded to the at least one polyamide skeleton via at least one linking group, such as bonded to any carbon or nitrogen of the polyamide skeleton via the at least one linking group. In one embodiment, the at least one linking group is chosen from single bonds and urea, urethane, thiourea, thiourethane, thioether, thioester, ester, ether and amine groups. For example, the at least one linking group is chosen from ureas, esters, and amines, and as a further example, is chosen from esters and amines. The bond is, for example, an ester bond. In one embodiment, these polymers comprise a fatty chain at each end of the polymer skeleton, such as the polyamide skeleton.

In one embodiment, due to the presence of at least one fatty chain, the polyamide polymers may be readily soluble in oils (i.e., water-immiscible liquid compounds) and thus may give macroscopically homogeneous compositions even with a high content (at least 25%) of the polyamide polymers, unlike certain polymers of the prior art that do not contain such alkyl or alkenyl chains at the end of the polyamide skeleton. As defined herein, a composition is soluble if it has a solubility of greater than 0.01 g per 100 ml of solution at 25° C.

In a further embodiment, the polyamide polymers can be chosen from polymers resulting from at least one polycondensation reaction between at least one acid chosen from dicarboxylic acids comprising at least 32 carbon atoms, such as 32 to 44 carbon atoms, and at least one amine chosen from diamines comprising at least 2 carbon atoms, such as from 2 to 36 carbon atoms, and triamines comprising at least 2 carbon atoms, such as from 2 to 36 carbon atoms. The dicarboxylic acids can, for example, be chosen from dimers of at least one fatty acid comprising at least 16 carbon atoms, such as oleic acid, linoleic acid and linolenic acid. The at least one amine can, for example, be chosen from diamines, such as ethylenediamine, hexylenediamine, hexamethylenediamine, phenylenediamine and triamines, such as ethylenetriamine.

The polyamide polymers may also be chosen from polymers comprising at least one terminal carboxylic acid group. The at least one terminal carboxylic acid group can, for example, be esterified with at least one alcohol chosen from monoalcohols comprising at least 4 carbon atoms. For example, the at least one alcohol can be chosen from monoalcohols comprising from 10 to 36 carbon atoms. In a further embodiment, the monoalcohols can comprise from 12 to 24 carbon atoms, such as from 16 to 24 carbon atoms, and for example 18 carbon atoms.

In certain embodiments, the at least one structuring polymer in the compositions of the present invention corresponds to the polyamide polymers of formula (I). Due to fatty chain (s), these polymers may be readily soluble in oils and thus lead to compositions that are macroscopically homogeneous even with a high content (at least 25%) of at least one structuring polymer. These polymers are described in U.S. Pat. No. 5,783,657:

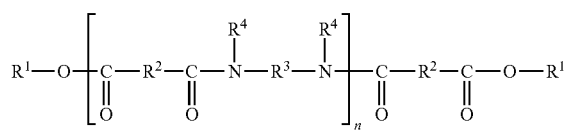

in which:
- n is an integer which represents the number of amide units such that the number of ester groups present in said at least one polyamide polymer ranges from 10% to 50% of the total number of all said ester groups and all said amide groups comprised in said at least one polyamide polymer;
- $R^1$, which are identical or different, are each chosen from alkyl groups comprising at least 4 carbon atoms and alkenyl groups comprising at least 4 carbon atoms. In one embodiment, the alkyl group comprises from 4 to 24 carbon atoms and the alkenyl group comprises from 4 to 24 carbon atoms;
- $R^2$, which are identical or different, are each chosen from $C_4$ to $C_{42}$ hydrocarbon-based groups with the proviso that at least 50% of all $R^2$ are chosen from $C_{30}$ to $C_{42}$ hydrocarbon-based groups;
- $R^3$, which are identical or different, are each chosen from organic groups comprising atoms chosen from carbon atoms, hydrogen atoms, oxygen atoms and nitrogen atoms with the proviso that $R^3$ comprises at least 2 carbon atoms; and
- $R^4$, which are identical or different, are each chosen from hydrogen atoms, $C_1$ to $C_{10}$ alkyl groups and a direct bond to at least one group chosen from $R^3$ and another $R^4$ such that when said at least one group is chosen from another $R^4$, the nitrogen atom to which both $R^3$ and $R^4$ are bonded forms part of a heterocyclic structure defined in part by $R^4$—N—$R^3$, with the proviso that at least 50% of all $R^4$ are chosen from hydrogen atoms.

In one embodiment, the at least one terminal fatty chain of formula (I) is linked to the last hetero atom, in this case nitrogen, of the polyamide skeleton. In a further embodiment, the terminal chains are functionalized. In another embodiment, the ester groups of formula (I), are linked to the terminal and/or pendant fatty chains, represent from 15% to 40% of the total number of ester and amide groups, such as, for example, from 20% to 35%.

In one embodiment, n may be an integer ranging from 1 to 5, for example, an integer ranging from 3 to 5. In the present invention, $R^1$, which are identical or different, can, for example, each be chosen from $C_{12}$ to $C_{22}$ alkyl groups, such as from $C_{16}$ to $C_{22}$ alkyl groups.

In the present invention, $R^2$, which are identical or different, can, for example, each be chosen from $C_{10}$ to $C_{42}$ alkyl groups. At least 50% of all $R^2$, which are identical or different, can, for example, each be chosen from groups comprising from 30 to 42 carbon atoms. At least 75% of all $R^2$, which are identical or different, can, for example, each be chosen from groups comprising from 30 to 42 carbon atoms. In the two aforementioned embodiments, the remaining $R^2$, which are identical or different, can, for example, each be chosen from $C_4$ to $C_{19}$ groups, such as $C_4$ to $C_{12}$ groups.

$R^3$, which can be identical or different, can, for example, each be chosen from $C_2$ to $C_{36}$ hydrocarbon-based groups and polyoxyalkylene groups. In another example, $R^3$, which can be identical or different, can each be chosen from $C_2$ to $C_{12}$ hydrocarbon-based groups. In another embodiment, $R^4$, which can be identical or different, can each be chosen from hydrogen atoms. As used herein, hydrocarbon-based groups may be chosen from linear, cyclic and branched, and saturated and unsaturated groups. The hydrocarbon-based groups can be chosen from aliphatic and aromatic groups. In one example, the hydrocarbon-based groups are chosen from aliphatic groups. The alkyl and alkylene groups may be chosen from linear, cyclic and branched, and saturated and unsaturated groups.

In general, the pendant and terminal fatty chains may be chosen from linear, cyclic and branched, and saturated and unsaturated groups. The pendant and terminal fatty chains can be chosen from aliphatic and aromatic groups. In one example, the pendant and terminal fatty chains are chosen from aliphatic groups.

According to the invention, the structuring of the liquid fatty phase is obtained with the aid of at least one structuring polymer, such as the at least one polymer of formula (I). The at least one polyamide polymer of formula (I) may, for example, be in the form of a mixture of polymers, and this mixture may also comprise a compound of formula (I) wherein n is equal to zero, i.e., a diester.

Non-limiting examples of at least one polyamide polymer that may be used in the compositions of the present invention include the commercial products sold by Arizona Chemical under the names Uniclear 80 and Uniclear 100. These are sold, respectively, in the form of an 80% (in terms of active material) gel in a mineral oil and a 100% (in terms of active material) gel. These polymers have a softening point ranging from 88° C. to 94° C., and may be mixtures of copolymers derived from monomers of (i) $C_{36}$ diacids and (ii) ethylenediamine, and have a weight-average molecular mass of about 6000. Terminal ester groups result from esterification of the remaining acid end groups with at least one alcohol chosen from cetyl alcohol and stearyl alcohol. A mixture of cetyl and stearyl alcohols is sometimes called cetylstearyl alcohol.

Other non-limiting examples of at least one polyamide polymer that may be used in the composition according to the present invention include polyamide polymers resulting from the condensation of at least one aliphatic dicarboxylic acid and at least one diamine, the carbonyl and amine groups being condensed via an amide bond. Examples of these polyamide polymers are those sold under the brand name Versamid by the companies General Mills Inc. and Henkel Corp. (Versamid 930, 744 or 1655) or by the company Olin Mathieson Chemical Corp. under the brand name Omamid, in particular Omamid S or C. These resins have a weight-average molecular mass ranging from 6000 to 9000. For further information regarding these polyamides, reference may be made to U.S. Pat. Nos. 3,645,705 and 3,148,125.

Other examples of polyamides include those sold by the company Arizona Chemicals under the references Uni-Rez (2658, 2931, 2970, 2621, 2613, 2624, 2665, 1554, 2623 and 2662) and the product sold under the reference Macromelt 6212 by the company Henkel. For further information regarding these polyamides, reference may be made to U.S. Pat. No. 5,500,209. Such polyamides display high melt viscosity characteristics. MACROMELT 6212, for example, has a high melt viscosity at 190° C. of 30-40 poise (as measured by a Brookfield Viscometer, Model RVF #3 spindle, 20 RPM).

In a further embodiment, the at least one polyamide polymer may be chosen from polyamide resins from vegetable sources. Polyamide resins from vegetable sources may be chosen from, for example, the polyamide resins disclosed in U.S. Pat. Nos. 5,783,657 and 5,998,570.

The structuring agent is typically present in the composition in an amount ranging from about 0.1% to about 80%, such as from about 2% to about 60%, further such as from about 5% to about 40%, and even further from about 5% to about 25% by weight relative to the total weight of the composition.

The at least one structuring polymer may have a softening point greater than 50° C., such as from 65° C. to 190° C., and further such as from 70° C. to 130° C., and even further such as from 80° C. to 105° C.

The Silicone Elastomer Powder

The silicone elastomer powders useful in this invention comprise particles of a globular or spherical core of cured silicone elastomer particle that, in general, have an average particle diameter from 0.1 µm to 100 µm, wherein the core is coated with a silicone resin e.g., a coating layer formed of a polyorganosilsesquioxane resin, which in general, is present in an amount of from 1 to 500 parts by weight per 100 parts by weight of the core silicone elastomer.

In certain embodiments, the silicone elastomer forming the core particles is a cured diorganopolysiloxane having linear diorganopolysiloxane segments represented by the general formula (II):

$(R—Si—O)_a$          (II);

wherein each R is, independently from the others, an unsubstituted or substituted monovalent hydrocarbon group having 1 to 20 carbon atoms exemplified by alkyl groups such as methyl, ethyl, propyl and butyl groups, aryl groups such as phenyl and tolyl groups, alkenyl groups such as vinyl and allyl groups and aralkyl groups such as 2-phenylethyl and 2-phenylpropyl groups as well as those substituted hydrocarbon groups obtained by replacing a part or all of the hydrogen atoms in the above named hydrocarbon groups with substituents including halogen atoms, epoxy group, amino group, mercapto group, (meth)acryloxy group and the like such as chloromethyl and 3,3,3-trifluoropropyl groups, at least 90% by moles of the groups R being preferably methyl groups, and the subscript a is a positive integer in the range of from 5 to 5000 such as from 10 to 1000.

The coated silicone elastomer particles can be prepared by in situ hydrolysis and condensation reaction of a trialkoxy silane compound in the presence of the cured silicone elastomer particles in an aqueous dispersion so as to form the coating layer of a silicone e.g., polyorganosilsesquioxane, resin on the surface of the silicone elastomer particles. The method of preparation includes admixing an aqueous dispersion of particles of a cured silicone elastomer having an average particle diameter in the range from 0.1 µm to 100 µm with an alkaline compound and a trialkoxy silane compound represented by the general formula (III):

$R'—Si(OR'')_3$          (III);

wherein R' is an unsubstituted or substituted monovalent hydrocarbon group, and R'' is an alkyl group having 1 to 6 carbon atoms, at a temperature not exceeding 60° C., and under agitation. Specific examples of the preparation of such silicone elastomer coated particles are described in U.S. Pat. No. 5,538,793. Examples of commercially available silicone elastomer particles coated with polyorganosilsesquioxane are available from Shin-Etsu and include the KSP-100 series, KSP-200 series and KSP-300 series. These are spherical particles of silicone elastomer coated with silicone resin, wherein the silicone elastomer core can be unfunctionalized for the KSP-100 series, functionalized with fluoroalkyl groups for the KSP-200 and functionalized with phenyl groups in the case of the KSP-300.

Swelling Agent

Swelling agents useful in the present invention include silicone oils chosen from volatile and non-volatile, linear and cyclic polydimethylsiloxanes (PDMSs) that are liquid at room temperature (e.g., cyclomethicones and dimethicones); polydimethylsiloxanes comprising alkyl or alkoxy groups which are pendant and/or at the end of the silicone chain, the groups each containing from 2 to 24 carbon atoms; phenyl-silicones such as phenyl trimethicones, phenyl dimethicones, phenyl trimethylsiloxy diphenylsiloxanes, diphenyl dimethicones, diphenyl methyldiphenyl trisiloxanes and 2-phenyl-ethyl trimethylsiloxysilicates, and fluorinated silicones. Some low-viscosity silicone oils useful in the present invention are linear polysiloxanes consisting (except for the terminal groups) of units of formula (IV): $[(R)_2—Si—O]$ in which each of the two substituents denoted "R" independently represents a lower alkyl group (having 1 to 6 C). The degree of polymerization (number of repeating units) of these low-viscosity polysiloxanes may range for example from about 3 to 2000. These low-viscosity silicone oils can be prepared according to known methods, or bought commercially: for example series 47 Silbione oil (RHONE POULENC), series 200 oil (DOW CORNING), SF 96 oil (GENERAL ELECTRIC). The terminal groups are, for example, trimethylsilyl, dimethyl hydroxymethylsilyl or vinyl dimethylsilyl groups.

The swelling agent must be cosmetically acceptable. Aside from that criterion, the choice of swelling agent depends on the chemical nature of the silicone elastomer core. For example, silicone elastomer cores having phenyl substituents (e.g., KSP-300) may be used with swelling agents such as a phenyltrimethicone, and cores having fluoro groups (e.g., KSP-200) may be used with agents such as fluorinated silicones. On the other hand, non-functionalized silicone elastomer cores (e.g., KSP-100) may be used with non-functionalized or functionalized swelling agents. Viscosity of the swelling agent generally varies from about 5 to 100,000 cst (centistokes). Agents having a relatively high viscosity will cause relatively slow swelling of the silicone elastomer powder, and agents having low viscosity will generally cause relatively fast swelling of the elastomer powder. More than one swelling agent may be used. In general, the swelling agent is present in the cosmetic composition in an amount of from about 0.1 to about 90%, and preferably from about 0.1 to about 40% by total weight of the composition. Relative amounts of silicone elastomer powder and swelling agent are determined based on the nature of the cosmetic composition. In general, the swelling agent will cause swelling of the elastomer powder in a range from about 10% of the original volume of the powder, to about 2.5 times or more the original volume (as measured, for example, by visual observation of a phase separation of unabsorbed swelling agent and the silicone elastomer core coated with the resin, in its swollen state).

Liquid Fatty Phase

The at least one liquid fatty phase, in one embodiment, may comprise at least one oil. The at least one oil, for example, may be chosen from polar oils and apolar oils including hydrocarbon-based liquid oils and oily liquids at room temperature. In one embodiment, the compositions of the invention comprise at least one structuring polymer and at least one polar oil. The fatty phase and the nature of the oil are selected to be chemically compatible with the structuring agent.

For a liquid fatty phase structured with an apolar polymer of the hydrocarbon-based type, this fatty phase may contain more than 30%, for example more than 40% by weight, or from 50% to 100% by weight, of at least one liquid apolar, such as hydrocarbon-based, oil, relative to the total weight of the liquid fatty phase.

For example, the at least one polar oil useful in the invention may be chosen from:
  hydrocarbon-based plant oils with a high content of triglycerides comprising fatty acid esters of glycerol in which the fatty acids may have varied chain lengths from $C_4$ to $C_{24}$, these chains possibly being chosen from linear and branched, and saturated and unsaturated chains; these oils are chosen from, for example, wheat germ oil, corn oil, sunflower oil, karite butter, castor oil, sweet almond oil, macadamia oil, apricot oil, soybean oil, cotton oil, alfalfa oil, poppy oil, pumpkin oil, sesame oil, marrow oil, rapeseed oil, avocado oil, hazelnut oil, grape seed oil, blackcurrant seed oil, evening primrose oil, millet oil, barley oil, quinoa oil, olive oil, rye oil, safflower oil, candlenut oil, passion flower oil and musk rose oil; or alternatively caprylic/capric acid triglycerides such as those sold by Stearineries Dubois or those sold under the names Miglyol 810, 812 and 818 by Dynamit Nobel;
  synthetic oils or esters of formula $R_5COOR_6$ in which $R_5$ is chosen from linear and branched fatty acid residues containing from 1 to 40 carbon atoms and $R_6$ is chosen from, for example, a hydrocarbon-based chain containing from 1 to 40 carbon atoms, on condition that $R_5+R_6 \geq 10$, such as, for example, purcellin oil (cetostearyl octanoate), isononyl isononanoate, $C_{12}$-$C_{15}$ alkyl benzoates, isopropyl myristate, 2-ethylhexyl palmitate, isostearyl isostearate and alkyl or polyalkyl octanoates, decanoates or ricinoleates; hydroxylated esters such as isostearyl lactate and diisostearyl malate; and pentaerythritol esters;
  synthetic ethers containing from 10 to 40 carbon atoms;
  $C_8$ to $C_{26}$ fatty alcohols such as oleyl alcohol; and
  $C_8$ to $C_{26}$ fatty acids such as oleic acid, linolenic acid or linoleic acid.

The at least one apolar oil according to the invention may include a hydrocarbon chosen from linear and branched, volatile and non-volatile hydrocarbons of synthetic and mineral origin, such as volatile liquid paraffins (such as isoparaffins and isododecane) or non-volatile liquid paraffins and derivatives thereof, liquid petrolatum, liquid lanolin, polydecenes, hydrogenated polyisobutene such as Parleam®, and squalane; silicone oils, polydimethylsiloxanes and phenyl-silicones that would otherwise not function herein as a swelling agent; and mixtures thereof. The structured oils, for example those structured with polyamides such as those of formula (I) or the polyurethanes or polyureas or polyurea-urethanes, may be, in one embodiment, apolar oils, such as an oil or a mixture of hydrocarbon oils chosen from those of mineral and synthetic origin, chosen from hydrocarbons such as alkanes such as Parleam® oil, isoparaffins including isododecane, and squalane, and mixtures thereof. These oils may, in one embodiment, be combined with at least one phenyl-silicone oil.

The liquid fatty phase, in one embodiment, contains at least one non-volatile oil chosen from, for example, hydrocarbon-based oils of mineral, plant and synthetic origin, synthetic esters or ethers, silicone oils and mixtures thereof.

In practice, the total liquid fatty phase may be present, for example, in an amount ranging from about 0.1% to about 99% by weight relative to the total weight of the composition; further examples include ranges of from about 5.0% to about 95.5%, from about 10% to about 80%, from about 20% to about 75%, and from about 1.0% to about 60% by weight relative to the total weight of the composition.

In addition to the liquid fatty phase, the cosmetic composition may also contain an aqueous phase, in which case, the cosmetic composition will be in the form of an emulsion. In these embodiments, the composition will also contain one or more emulsifiers to facilitate formation and stability of an emulsion. Examples of aqueous emulsions include oil-in-water emulsions, water-in-oil emulsions and multiple emulsions such as oil-in-water-in-oil emulsions and water-in-oil-in-water emulsions. However, the compositions of the present invention are not limited to emulsions that contain an aqueous phase. Compositions may also be in the form of an anhydrous emulsion, (e.g., they may contain a polyol such as glycerin and propylene glycol).

Emulsifiers

Examples of organic emulsifiers include any ethoxylated surfactants known in the art such as Polysorbate-20, Laureth-7, Laureth-4, Sepigel® 305 available from SEPPIC and other similar ingredients disclosed in the *International Cosmetic Ingredient Dictionary and Handbook Vol.* 4 ($9^{th}$ ed. 2002), more particularly the emulsifiers disclosed on pages 2962-2971. Examples of organosilicone emulsifiers include cetyl dimethicone copolyol-polyglyceryl-4-isostearate-hexylaurate (ABIL® WE 09) available from Goldschmidt Chemical Corporation, Cetyl Dimethicone Copolyol (ABIL® EM 90), (ABIL® EM 97), Laurylmethicone Copolyol (5200), Cyclomethicone (and) Dimethicone Copolyol (DC 5225 C and DC 3225 C) available from GE Silicones, Cyclopentasiloxane & Dimethicone Copolyol (GE SF 1528) or any other formulation aids known to persons skilled in the art. Other fatty substances useful as formulation aids include but are not limited to, silicones in esterified or unesterified liquid form or in esterified solid form, such as behenate dimethicone; and non-silicone fatty substances including oils such as vegetable and mineral oil; animal and/or synthetic waxes such as beeswax, paraffin, rice bran wax, candelilla wax, carnauba wax and derivatives thereof; and hydrocarbon gels or bentone type gels, such as Gel SS71, Gel EA2786, Quaternium-18 Bentonite, 38 CE, Gel ISD V or Gel ISD. Other emulsifiers may include sugar derivatives such as alkylpolyglucosides or sugar esters. Also used as emulsifiers include ethoxylated stearates such as polyglyceryl-2 dipolyhydroxystearate, or polyglyceryl-10 polyhydroxystearate or PEG-30 dipolyhydroxystearate.

These substances may be included in the compositions of the present invention to affect properties such as consistency and texture.

Film-forming Polymer

One or more film-forming polymers may be present in the composition, provided that they are compatible with it (e.g., do not cause phase separation). Appropriate amounts of the film former may be determined by one of skill in the art and can vary considerably based on the application. For example, for cosmetic compositions, the film former may be used in an amount from 0.1% to 20% such as, for example, from 1% to 10% by weight, relative to the total weight of the composition.

In one embodiment, the film-forming silicone resin is chosen from silsesquioxanes and siloxysilicates. Representative examples of such silsesquioxane film formers may include Belsil PMS MK, also referred to as Resin MK, available from Wacker Chemie, KR-220L, KR-242A, or KR-251 available from SHIN-ETSU. Examples of siloxysilicate film formers may include Wacker 803 and 804 available from Wacker Silicones Corporation, G.E. 1170-002 available from General Electric, diisostearoyl trimethylolpropane siloxysilicates, such as SF 1318, available from GE Silicones. High viscosity phenylated silicone such as phenyltrimethicone available as Belsil PDM 1000 may be used as a silicone based film former.

In another embodiment the film former may be a compound obtained by the reaction of silicone moieties with ethylenically unsaturated monomers. The resulting copolymers may be graft or block copolymers comprising at least one backbone and at least one chain, wherein at least one of the at least one backbone and at least one chain is chosen from silicones. In an embodiment, the at least one copolymer is chosen from copolymers comprising at least one polar backbone and at least one non-polar chain and copolymers comprising at least one non-polar backbone and at least one polar chain, wherein at least one of the at least one backbone and at least one chain is chosen from silicones.

In an embodiment, the at least one copolymer is chosen from copolymers comprising a polymer skeleton comprising at least one non-polar, silicone backbone substituted with at least one polar, non-silicone chain and copolymers comprising a polymer skeleton comprising at least one polar, non-silicone backbone substituted with at least one non-polar, silicone chain.

In another embodiment, the at least one copolymer is chosen from copolymers comprising a polymer skeleton comprising at least one polar, silicone backbone substituted with at least one non-polar, non-silicone chain and copolymers comprising a polymer skeleton comprising at least one non-polar, non-silicone backbone substituted with at least one polar, silicone chain.

In an embodiment, the at least one polar chain comprises at least one ester group. In another embodiment, the at least one polar chain comprises at least one ester group and at least one double bond. In another embodiment, the at least one polar, non-silicone backbone is chosen from acrylate polymers, methacrylate polymers, and vinyl polymers.

In another embodiment, the at least one copolymer further comprises at least one hydrocarbon group. In an embodiment, the at least one hydrocarbon group is a terminal hydrocarbon group bonded to the polymer skeleton. In another embodiment, the at least one hydrocarbon group is a pendant hydrocarbon group bonded to the polymer skeleton. In another embodiment, the at least one hydrocarbon group is a terminal hydrocarbon group bonded to at least one chain on the polymer skeleton. In another embodiment, the hydrocarbon group is a pendant hydrocarbon group bonded to at least one chain on the polymer skeleton. Non-limiting examples of the at least one hydrocarbon group include $C_5$-$C_{25}$ alkyl groups, optionally substituted, such as $C_{18}$ alkyl groups and $C_{22}$ alkyl groups.

Non-limiting examples of the at least one copolymer include silicone/(meth)acrylate copolymers, such as those as described in U.S. Pat. Nos. 5,061,481, 5,219,560, and 5,262,087. Further non-limiting examples of the at least one copolymer are non-polar silicone copolymers comprising repeating units of at least one polar (meth)acrylate unit and vinyl copolymers grafted with at least one non-polar silicone chain. Non-limiting examples of such copolymers are acrylates/stearyl acrylate/dimethicone acrylates copolymers, such as those commercially available from Shin-Etsu, for example, the product sold under the tradename KP-561, and acrylates/behenyl acrylate/dimethicone acrylates copolymer, such as those commercially available from Shin-Etsu, for example, the product sold under the tradename KP-562.

Another non-limiting example of at least one copolymer suitable for use in the present invention are silicone esters comprising units of formulae (V) and (VI), disclosed in U.S. Pat. Nos. 6,045,782, 5,334,737, and 4,725,658:

  (V); and

  (VI);

wherein
R and R', which may be identical or different, are each chosen from optionally substituted hydrocarbon groups;
a and b, which may be identical or different, are each a number ranging from 0 to 3, with the proviso that the sum of a and b is a number ranging from 1 to 3,
x and y, which may be identical or different, are each a number ranging from 0 to 3, with the proviso that the sum of x and y is a number ranging from 1 to 3;
$R^E$, which may be identical or different, are each chosen from groups comprising at least one carboxylic ester.

In an embodiment, $R^E$ groups are chosen from groups comprising at least one ester group formed from the reaction of at least one acid and at least one alcohol. In an embodiment, the at least one acid comprises at least two carbon atoms. In another embodiment, the at least one alcohol comprises at least ten carbon atoms. Non-limiting examples of the at least one acid include branched acids such as isostearic acid, and linear acids such as behenic acid. Non-limiting examples of the at least one alcohol include monohydric alcohols and polyhydric alcohols, such as n-propanol and branched etheralkanols such as (3,3,3-trimethylolpropoxy)propane.

Further non-limiting examples of the at least one copolymer include liquid sioxy silicates and silicone esters such as those disclosed in U.S. Pat. No. 5,334,737, such as diisostearoyl trimethylolpropane siloxysilicate and dilauroyl trimethylolpropane siloxy silicate, which are commercially available from General Electric under the tradenames SF 1318 and SF 1312, respectively.

Further non-limiting examples of the at least one copolymer include polymers comprising a backbone chosen from vinyl polymers, methacrylic polymers, and acrylic polymers and at least one chain chosen from pendant siloxane groups and pendant fluorochemical groups. Non-limiting examples of such polymers comprise at least one unit derived from at least one A monomer, at least one unit derived from at least one C monomer, at least one unit derived from D monomers, and, optionally, at least one unit derived from at least one B monomer, wherein:

A, which may be identical or different, are each chosen from free-radically-polymerizable acrylic esters of at least one alcohol chosen from 1,1-dihydroperfluoroalkanols, omega-hydridofluoroalkanols, fluoroalkylsulfonamido alcohols, cyclic fluoroalkyl alcohols, and fluoroether alcohols, and analogs of any of the foregoing at least one alcohols, and free-radically-polymerizable methacrylic esters of at least one alcohol chosen from 1,1,-dihydroperfluoroalkanols, omega-hydridofluoroalkanols, fluoroalkylsulfonamido alcohols, cyclic fluoroalkyl alcohols, and fluoroether alcohols, and analogs of any of the foregoing at least one alcohols;

B, which may be identical or different, are each chosen from reinforcing monomers which are copolymerizable with at least one A monomer;

C, which may be identical or different, are each chosen from monomers represented by formula (VII):

wherein

X is chosen from vinyl groups which are copolymerizable with at least one A monomer and at least one B monomer, Y is chosen from divalent allylene groups, divalent arylene groups, divalent alkarylene groups, and divalent aralkylene groups, wherein the groups comprise from 1 to 30 carbon atoms, and further wherein the groups optionally further comprise at least one group chosen from ester groups, amide groups, urethane groups, and urea groups;

n is zero or 1;

m is a number ranging from 1 to 3;

R, which may be identical or different, are each chosen from hydrogen, $C_1$-$C_4$ alkyl groups, aryl groups, and alkoxy groups; and Z, which may be identical or different, are each chosen from monovalent siloxane polymeric groups; and D, which may be identical or different, are each chosen from free-radically-polymerizable acrylate copolymers and free-radically-polymerizable methacrylate copolymers. Such polymers and their manufacture are disclosed in U.S. Pat. Nos. 5,209,924 and 4,972,037, and WO 01/32737.

Further non-limiting examples of the at least one copolymer include polymers comprising at least one A monomer, at least one C monomer, and at least one D monomer, wherein A, which may be identical or different, are each chosen from polymerizable acrylic esters of at least one fluoroalkylsulfonamido alcohol and polymerizable methacrylic esters of at least one fluoroalkylsulfonamido alcohol, D, which may be identical or different, are each chosen from methacrylic acid esters of at least one $C_1$-$C_{12}$ linear alcohol and methacrylic acid esters of at least one $C_1$-$C_{12}$ branched alcohol, and C is as defined above in preceding paragraphs. Such polymers include polymers comprising at least one group represented by formula (VIII):

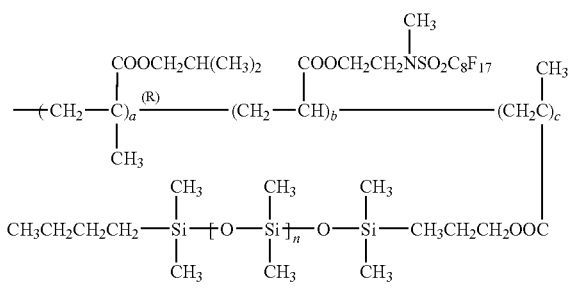

wherein a, b, and c, which may be identical or different, are each a number ranging from 1 to 100,000; and the terminal groups, which may be identical or different, are each chosen from $C_1$-$C_{20}$ linear alkyl groups, $C_3$-$C_{20}$ branched chain alkyl groups, $C_3$-$C_{20}$ aryl groups, $C_1$-$C_{20}$ linear alkoxy groups, and $C_3$-$C_{20}$ branched alkoxy groups. Such polymers are disclosed in U.S. Pat. Nos. 4,972,037, 5,061,481, 5,209,924, 5,849,275, and 6,033,650. These polymers may be purchased from Minnesota Mining and Manufacturing Company under the tradenames "Silicone Plus" polymers. For example, poly (isobutyl methacrylate-co-methyl FOSEA)-g-poly (dimethylsiloxane) is sold under the tradename SA 70-5 IBMMF.

Other non-limiting examples of the at least one copolymer is silicone/acrylate graft terpolymers, for example, those represented by formula (IX):

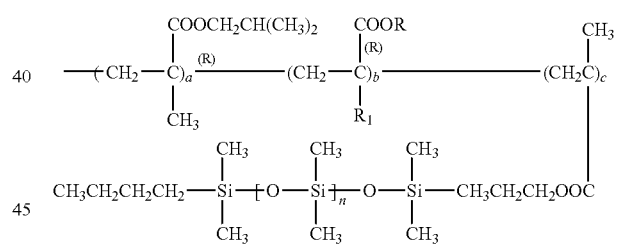

wherein a, b, and c are present in a weight ratio of 69.9:0.1:30 respectively,

R and $R^1$, which may be identical or different, are each chosen from hydrogen and $C_1$-$C_6$ alkyl groups; and m is a number ranging from 100-150. In an embodiment, m is chosen to provide a macromer having a molecular weight ranging from 8,000 to 12,000, such as 10,000. In another embodiment, m is a number ranging from 124-135, such as 130. Non-limiting examples of these copolymers are described in WO 01/32727 A1.

In another embodiment of the invention, the at least one copolymer comprises a backbone chosen from vinyl backbones, methacrylic backbones, and acrylic polymeric backbones and further comprises at least one pendant siloxane group. Non-limiting examples of such polymers are disclosed in U.S. Pat. Nos. 4,693,935, 4,981,903 and 4,981,902.

In an embodiment, the at least one copolymer comprises at least one A monomer, at least one C monomer, and, optionally at least one B monomer, wherein the at least one A monomer is chosen from free-radically-polymerizable vinyl monomers, free-radically-polymerizable methacrylate monomers, and free-radically-polymerizable acrylate monomers; the at least one B monomer, if present, is chosen from at least one reinforcing monomer copolymerizable with the at least one A monomer, and the at least one C monomer is chosen from monomers represented by formula (X):

$$X(Y)_n Si(R)_{3-m} Z_m \qquad (X)$$

wherein:
X is chosen from vinyl groups which are copolymerizable with the at least one A monomer and with the at least one B monomer;
Y is chosen from divalent groups;
n is zero or 1;
m is a number ranging from 1 to 3;
R, which may be identical or different, are each chosen from hydrogen, optionally substituted $C_1$-$C_{10}$ alkyl groups, optionally substituted phenyl groups, and optionally substituted $C_1$-$C_{10}$ alkoxy groups; and
Z, which may be identical or different, are each chosen from monovalent siloxane polymeric groups. Non-limiting examples of A monomers include methacrylic acid esters of $C_1$-$C_{12}$ linear alcohols, methacrylic acid esters of $C_1$-$C_{12}$ of branched alcohols, styrene monomers, vinyl esters, vinyl chloride monomers, vinylidene chloride monomers, and acryloyl monomers. Non-limiting examples of B monomers include acrylic monomers comprising at least one group chosen from hydroxyl, amino, and ionic groups, and methacrylic monomers comprising at least one group chosen from hydroxyl, amino, and ionic groups. Non-limiting examples of ionic groups include quaternary ammonium groups, carboxylate salts, and sulfonic acid salts. The C monomers are as above defined above in preceding paragraphs.

In another embodiment of the invention, the at least one co-polymer is chosen from vinyl-silicone graft copolymers having the following formula and vinyl-silicone block copolymers represented by formula (XI):

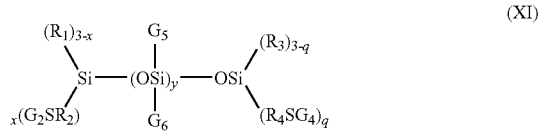

wherein
$G_5$, which may be identical or different, are each chosen from alkyl groups, aryl groups, aralkyl groups, alkoxy groups, alkylamino groups, fluoroalkyl groups, hydrogen, and -ZSA groups, wherein
A is chosen from vinyl polymeric segments comprising at least one polymerized free-radically-polymerizable monomer, and
Z is chosen from divalent $C_1$-$C_{10}$ alkylene groups, divalent aralkylene groups, divalent arylene groups, and divalent alkoxylalkylene groups. In an embodiment Z is chosen from methylene groups and propylene groups.
$G_6$, which may be identical or different, are each chosen from alkyl groups, aryl groups, aralkyl groups, alkoxy groups, alkylamino groups, fluoroalkyl groups, hydrogen, and -ZSA groups, as defined above;
$G_2$ comprises A;
$G_4$ comprises A;
$R_1$, which may be identical or different, are each chosen from alkyl groups, aryl groups, aralkyl groups, alkoxy groups, alkylamino groups, fluoroalkyl groups, hydrogen, and hydroxyl. In one embodiment, $R_1$ is chosen from $C_1$-$C_4$ alkyl groups, such as methyl groups, and hydroxyl.
$R_2$, which may be identical or different, are each chosen from divalent $C_{1-10}$ alkylene groups, divalent arylene groups, divalent aralkylene groups, and divalent alkoxyalkylene groups. In one embodiment, $R_2$ is chosen from divalent $C_1$-$C_3$ alkylene groups and divalent $C_7$-$C_{10}$ aralkylene groups. In another embodiment, $R_2$ is chosen from —$CH_2$— groups and divalent 1,3-propylene groups.
$R_3$, which may be identical or different, are each chosen from alkyl groups, aryl groups, aralkyl groups alkoxy groups, alkylamino groups, fluoroalkyl groups, hydrogen, and hydroxyl. In one embodiment, $R_3$ is chosen from $C_1$-$C_4$ alkyl groups and hydroxyl. In another embodiment, $R_3$ is chosen from methyl groups.
$R_4$, which may be identical or different, are each chosen from divalent $C_1$-$C_{10}$ alkylene groups, divalent arylene groups, divalent aralkylene groups, and divalent alkoxyalkylene groups. In one embodiment, $R_4$ is chosen from divalent $C_1$-$C_3$ alkylene groups and divalent $C_7$-$C_{10}$ aralkylene groups. In another embodiment, $R_4$ is chosen from divalent —$CH_2$— groups and divalent 1,3-propylene groups.
x is a number ranging from 0 to 3;
y is a number greater than or equal to 5. In an embodiment, y ranges from 10 to 270, and in another embodiment, y ranges from 40 to 270.
q is a number ranging from 0 to 3;

Non-limiting examples of these polymers are described in U.S. Pat. No. 5,468,477. A non-limiting example of such polymers is poly(dimethylsiloxane)-g-poly(isobutyl methacrylate), which is commercially available from 3M Company under the tradename VS 70 IBM.

In an embodiment, the at least one copolymer is present in the composition in an amount ranging from 0.1% to 20% by weight relative to the total weight of the composition. In another embodiment, the at least one copolymer is present in an amount ranging from 1% to 10% by weight relative to the total weight of the composition. One of ordinary skill in the art will recognize that the at least one copolymer according to the present invention may be commercially available, and may come from suppliers in the form of a dilute solution. The amounts of the at least one copolymer disclosed herein therefore reflect the weight percent of active material.

Other film forming polymers may also be a other non silicone film formers. These non silicone film formers may be chosen from, for example, polyethylene; vinylpyrrolidone/vinyl acetate (PVP/VA) copolymers such as the Luviskol® VA grades (all ranges) from BASF® Corporation and the PVP/VA series from ISP; acrylic fluorinated emulsion film formers including Foraperle® film formers such as Foraperle® 303 D from Elf Atochem (although Foraperle® may not be appropriate for some cosmetic formulations); GANEX® copolymers such as butylated PVP, PVP/Hexadecene copolymer, PVP/Eicosene copolymer or tricontanyl; Poly(vinylpyrrolidone/diethylaminoethyl methacrylate) or PVP/Dimethylaminoethylmethacrylate copolymers such as Copolymer 845; Resin ACO-5014 (Imidized 1B/MA copolymer); other PVP based polymers and copolymers; alkyl cycloalkylacrylate copolymers (See WO 98/42298, the disclosure of which is hereby incorporated by reference); Mexomere® film formers and other allyl stearate/vinyl acetate copolymers (allyl stearate/VA copolymers); polyolprepolymers such as PPG-12/SMDI copolymer, polyolprepolymers such as PPG-1 2/SM D1 copolymer, Poly(oxy-1,2-ethanediyl), α-hydro-ω-hydroxy-polymer with 1,1'-methylene-bis-(4-isocyanatocyclohexane) available from Barnet; Avalure™ AC Polymers (Acrylates Copolymer) and Avalure™ UR polymers (Polyurethane Dispersions), available from BFGoodrich.

The film former which also may be used within the framework of the invention includes film formers having any film former chemistry known in the art such as: PVP, acrylates, and urethanes; synthetic polymers of the polycondensate type or free-radical type, or ionic type, polymers of natural origin and mixtures thereof or any other film former known within the practice of the cosmetic and pharmaceutical arts which one skilled in the art may determine to be compatible. Film formers that may be used are also disclosed in the *International Cosmetic Ingredient Dictionary and Handbook Vol. 2* (7$^{th}$ ed. 1999), more particularly the emollients disclosed on pages 1636-1638.

Waxes

One or more waxes may be present in the compositions, once again, provided that they are compatible with the composition. As used herein, a "wax" may be any lipophilic fatty compound. Examples of waxes that may be useful in the present invention include waxes of natural origin, such as beeswax, carnauba wax, candelilla wax, ouricury wax, Japan wax, cork fiber wax, sugar cane wax, paraffin waxes, lignite wax, microcrystalline waxes, lanolin wax, montan wax and ozokerites, hydrogenated oils such as hydrogenated jojoba oil, jojoba esters, waxes of synthetic origin, such as polyethylene waxes derived from polymerization of ethylene, waxes obtained by Fischer-Tropsch synthesis, fatty acid esters and glycerides, and silicone waxes such as derivatives of poly(di)methylsiloxane. In general, the wax is present in an amount ranging from about 0.01% to about 15%, and preferably from about 0.1% to about 10% relative to the total weight of the cosmetic composition.

Sunscreens

The cosmetic compositions of this invention may also comprise sunscreens which are chemical absorbers actually absorb harmful ultraviolet radiation. It is well known that chemical absorbers are classified, depending on the type of radiation they protect against, as either UV-A or UV-B absorbers. UV-A absorbers generally absorb radiation in the 320 to 400 nm region of the ultraviolet spectrum. UV-A absorbers include anthranilates, benzophenones, and dibenzoyl methanes. UV-B absorbers generally absorb radiation in the 280 to 320 nm region of the ultraviolet spectrum. UV-B absorbers include p-aminobenzoic acid derivatives, camphor derivatives, cinnamates, and salicylates.

Classifying the chemical absorbers generally as UV-A or UV-B absorbers is accepted within the industry. However, a more precise classification is one based upon the chemical properties of the sunscreens. There are eight major classifications of sunscreen chemical properties which are discussed at length in "Sunscreens—Development, Evaluation and Regulatory Aspects," by N. Shaath et al., 2nd. Edition, pages 269-273, Marcel Dekker, Inc. (1997).

The sunscreens useful in the present invention typically comprise chemical absorbers, but may also comprise physical blockers. Exemplary sunscreens which may be formulated into the compositions of the present invention are chemical absorbers such as p-aminobenzoic acid derivatives, anthranilates, benzophenones, camphor derivatives, cinnamic derivatives, dibenzoyl methanes (such as avobenzone also known as Parsol®1789), diphenylacrylate derivatives, salicylic derivatives, triazine derivatives, benzimidazole compounds, bis-benzoazolyl derivatives, methylene bis-(hydroxyphenylbenzotriazole) compounds, the sunscreen polymers and silicones, or mixtures thereof. These are variously described in U.S. Pat. Nos. 2,463,264, 4,367,390, 5,166,355 and 5,237,071 and in EP 863,145, EP 517,104, EP 570,838, EP 796,851, EP 775,698, EP 878,469, EP 933,376, EP 893,119, EP 669,323, GB 2,303,549, DE 1,972,184 and WO 93/04665. Also exemplary of the sunscreens which may be formulated into the compositions of this invention are physical blockers such as cerium oxides, chromium oxides, cobalt oxides, iron oxides, red petrolatum, silicone-treated titanium dioxide, titanium dioxide, zinc oxide, and/or zirconium oxide, or mixtures thereof.

A wide variety of sunscreens is described in U.S. Pat. Nos. 5,087,445 and 5,073,372, and Chapter VIII of *Cosmetics and Science and Technology* (1957) by Segarin et al., pages 189 et seq.

Sunscreens which may be formulated into the compositions of the instant invention are those selected from among: aminobenzoic acid, amyldimethyl PABA, cinoxate, diethanolamine p-methoxycinnamate, digalloyl trioleate, dioxybenzone, 2-ethoxyethyl p-methoxycinnamate, ethyl 4-bis (hydroxypropyl)aminobenzoate, 2-ethylhexyl-2-cyano-3,3-diphenylacrylate, ethylhexyl p-methoxycinnamate, 2-ethylhexyl salicylate, glyceryl aminobenzoate, homomenthyl salicylate, homosalate, 3-imidazol-4-ylacrylic acid and ethyl ester, methyl anthranilate, octyldimethyl PABA, 2-phenylbenzimidazole-5-sulfonic acid and salts, red petrolatum, sulisobenzone, titanium dioxide, triethanolamine salicylate, N,N,N-trimethyl-4-(2-oxoborn-3-ylidene methyl)anillinium methyl sulfate, and mixtures thereof.

Sunscreens active in the UV-A and/or UV-B range can also include:

p-aminobenzoic acid,
oxyethylene (25 mol) p-aminobenzoate,
2-ethylhexyl p-dimethylaminobenzoate,
ethyl N-oxypropylene p-aminobenzoate,
glycerol p-aminobenzoate,
4-isopropylbenzyl salicylate,
2-ethylhexyl 4-methoxycinnamate,
methyl diisopropylcinnamate,
isoamyl 4-methoxycinnamate,
diethanolamine 4-methoxycinnamate,
3-(4'-trimethylammunium)-benzyliden-bornan-2-one methylsulfate,
2-hydroxy-4-methoxybenzophenone,
2-hydroxy-4-methoxybenzophenone-5-sulfonate,
2,4-dihydroxybenzophenone,
2,2',4,4'-tetrahydroxybenzophenone,
2,2'-dihydroxy-4,4'dimethoxybenzophenone, 2-hydroxy-4-n-octoxybenzophenone,
2-hydroxy-4-methoxy-4'-methoxybenzophenone,
-(2-oxoborn-3-ylidene)-tolyl-4-sulfonic acid and soluble salts thereof,
3-(4'-sulfo)benzyliden-bornan-2-one and soluble salts thereof,
3-(4'methylbenzylidene)-d,l-camphor,
3-benzylidene-d,l-camphor, benzene 1,4-di(3-methylidene-10-camphosulfonic) acid and salts thereof (the product Mexoryl SX described in U.S. Pat. No. 4,585,597, urocanic acid, 2,4,6-tris[p-(2'-ethylhexyl-1'-oxycarbonyl)-anilino]-1,3,5-triazine, 2-[(p-(tertiobutylamido)anilino]-4,6-bis-[(p-(2'-ethylhexyl-1'-oxycarbonyl)anilino]-1,3,5-triazine, 2,4-bis{[4-(2-ethyl-hexyloxy)]-2-hydroxy]-phenyl}-6-(4-methoxy-phenyl)-1,3,5-triazine ("TINOSORB S" marketed by Ciba), the polymer of N-(2 et 4)-[(2-oxoborn-3-yliden)methyl]benzyl]-acrylamide, 1,4-bisbenzimidazolyl-phenylen-3,3',5,5'-tetrasulfonic acid and salts thereof, the benzalmalonate-substituted polyorganosiloxanes, the benzotriazole-substituted polyorganosiloxanes (Drometrizole Trisiloxane), dispersed 2,2'-methylene-bis-[6-(2H-benzotriazol-2-yl)-4-(1,1,3,3-tetramethylbutyl)phenol] such as that marketed under the trademark MIXXIM BB/100 by Fairmount Chemical, or micronized in dispersed form thereof such as that were marketed under the trademark TINOSORB M by Ciba Specialty Chemicals Corp. (Tarrytown, N.Y.), and solubilized 2,2'-methylene-bis-[6-(2H-benzotriazol-2-yl)-4-(methyl)phenol] such as that marketed under the trademark MIXXIM BB/200 by Fairmount Chemical.

Typically combinations of one or more of these sunscreens are used.

The dibenzoyl methane derivatives other than avobenzone are described, for example, in FR 2,326,405, FR 2,440,933 and EP 114,607.

Other dibenzoyl methane sunscreens other than avobenzone include (whether singly or in any combination):

2-methyldibenzoylmethane
4-methyldibenzoylmethane
4-isopropyldibenzoylmethane
4-tert-butyldibenzoylmethane
2,4-dimethyldibenzoylmethane
2,5-dimethyldibenzoylmethane
4,4'-diisopropyldibenzoylmethane
4,4'-dimethoxydibenzoylmethane
2-methyl-5-isopropyl-4'-methoxydibenzoylmethane
2-methyl-5-tert-butyl-4'-methoxydibenzoylmethane
2,4-dimethyl-4'-methoxydibenzoylmethane
2,6-dimethyl-4-tert-butyl-4'-methoxydibenzoylmethane Additional sunscreens that can be used are described in pages 2954-2955 of the *International Cosmetic Ingredient Dictionary and Handbook* (9$^{th}$ ed. 2002).

Plasticizers

Plasticizers may also be added to the compositions to improve the flexibility and cosmetic properties of the resulting formulation. Plasticizers are materials that soften synthetic polymers. They are frequently required to avoid brittleness and cracking of film formers. One skilled in the art may routinely vary the amount of plasticizer desired based on the properties desired and the application envisaged. Plasticizers useful in the practice of the invention include lecithin, polysorbates, dimethicone copolyol, glycols, citrate esters, glycerin, dimethicone, and other similar ingredients disclosed in the *International Cosmetic Ingredient Dictionary and Handbook Vol.* 4 (9$^{th}$ ed. 2002), more particularly the plasticizers disclosed on page 2927.

Other Additives

The composition of the present invention may also further comprise at least one suitable (e.g., cosmetically or dermatologically acceptable) additive commonly used in the field concerned chosen from coloring agents (e.g., pigments), anti-oxidants, essential oils, preserving agents, fragrances, fillers, pasty fatty substances, waxy fatty substances, neutralizing agents, lipo-soluble polymers, and cosmetically active agents and dermatological active agents such as, for example, emollients, moisturizers, vitamins and essential fatty acids. The compositions of the invention may also be optionally thickened with an aqueous-phase thickener or gelled with a gelling agent and/or containing ingredients soluble in water. In embodiments where the cosmetic compositions are colored due to the presence of at least one pigment, the pigment is preferably treated, e.g., with an amino acid. Treated pigments are known in the art. See, e.g., U.S. Pat. No. 5,843,417. For example, pigments treated with silicones are described in U.S. Pat. No. 4,574,082, and pigments treated with amino acids are described in U.S. Pat. No. 4,606,914. Treated pigments are commercially available from U.S. Cosmetics Corp., a distributor of Miyoshi Kasei (Japan) (e.g., pigments treated with a vegetable-derived amino acid such as disodium stearoyl glutamate, aluminum oxide and optionally titanium dioxide).

The invention will be further described by reference to the detailed examples. These examples are provided for purposes of illustration only, and are not intended to be limiting unless otherwise specified.

Example 1

Foundation

| Phase | Trade Name | INCI Name | % w/w |
|---|---|---|---|
| A1 | Uniclear 100 | Polyamide | 3.00 |
|  | Octyldodecanol | Octyldodecanol | 3.70 |
|  | Finsolv TN | C12-C15 Alkyl Benzoate | 3.60 |
|  | Parsol MCX | Ethylhexyl Methoxycinnamate | 4.00 |
|  | Wickenol 151 | Isononyl Isononanoate | 7.60 |
| A2 | VEGETABLE AMINO ACID AND ALUMINUM HYDROXIDE TREATED PIGMENTS (AVAILABLE FROM U.S. COSMETICS CORP.) | Amino acid-treated pigments | 12.00 |
| A3 | Arlacel P135 | PEG-30 Dipolyhydroxystearate | 2.00 |
| A4 | Butylparaben | Butylparaben | 0.30 |
|  | Bentone 38V | Disteardimonium Hectorite | 1.20 |
| A5 | DC 245 Fluid | Cyclopentasiloxane | 5.00 |
| A6 | GANZPEARL GMX-0610 | MMA Crosspolymer | 2.50 |
|  | CERIDUST 9205 F | PTFE | 0.50 |
|  | ORGASOL 2002 | Nylon-12 | 1.00 |
|  | CARDRE MICA 8 | Mica | 1.00 |
|  | KSP-100 | Vinyl Dimethicone/ Methicone Silsesquioxane Crosspolymer | 3.00 |
| A7 | PERMETHYL 99A | Isododecane | 11.00 |
| B | Water | Water | 35.20 |
|  | 1,3-Butylene Glycol | Butylene Glycol | 2.00 |

-continued

| Phase | Trade Name | INCI Name | % w/w |
|---|---|---|---|
| | Magnesium Sulfate | Magnesium Sulfate | 0.60 |
| | Methylparaben | Methylparaben | 0.20 |
| | Phenoxyethanol | Phenoxyethanol | 0.60 |
| | | Total: | 100.00 |

Example 2

Foundation

| Ingredient | % w/w |
|---|---|
| Phase A | |
| Structuring polymer Uniclear 100 | 5.00 |
| Fatty Alcohol | 3.00 |
| Emollient Esters | 7.00 |
| PEG-30 Dihydroxystearate: Arlacel P135 | 2.00 |
| Preservative | 0.20 |
| Disteardimonium Hectorite Bentone 38V | 1.40 |
| Phase B | |
| Silicone elastomer powder KSP-100 | 3.60 |
| Dimethicone DC 200 Fluid 10 Cst | 8.40 |
| Methyl Methacrylate Crosspolymer, Ganzpearl GMX-0610 | 4.00 |
| Phase C | |
| Isododecane | 16.60 |
| Phase D | |
| Water | 29.20 |
| Butylene Glycol | 3.00 |
| Polyquaternium-10, UCARE Polymer JR 125 | 0.10 |
| Magnesium Sulfate | 0.70 |
| Water soluble preservatives | 0.80 |
| Phase E | |
| Emollient Ester | 5.00 |
| Amino acid treated Pigments | 10.00 |

To make this composition, phase A was heated at the temperature of 80-85° C. for about 15 minutes or until the Uniclear polymer was dissolved, while mixing to achieve uniformity. Phase B was added, while mixing under sheer to achieve good pigment dispersion. Phases C, D, E and F were added sequentially, while mixing. Phase G was then added slowly at a temperature of about 70-75° C. under homogenization, to form an emulsion. This foundation had a silky feel.

Example 3

Make-Up as a Water-in-Oil (W/O) Emulsion

| Phase | Ingredients | % W/W |
|---|---|---|
| A | Structuring polymer Uniclear 100 | 3.00 |
| | Octyldodecanol | 3.70 |
| | C12-C15 Benzoate | 3.60 |
| | Ethylhexyl Methoxycinnamate | 4.00 |
| | Isononyl Isononanoate | 7.60 |
| | PEG-30 Dipolyhydroxystearate | 2.00 |
| B | Amino acid treated pigment | 12.0 |

-continued

| Phase | Ingredients | % W/W |
|---|---|---|
| C | Dimethicone DC 200 Fluid | 6.00 |
| | Vinyl dimethicone/methicone silsesquioxane crosspolymer | 3.00 |
| D | Butylparaben | 0.30 |
| | Disteardimonium Hectorite | 1.20 |
| E | Cyclopentasiloxane | 5.00 |
| | Isododecane | 11.00 |
| F | Methyl methacrylate (MMA) Crosspolymer | 2.50 |
| | PTFE | 0.50 |
| | Nylon-12 | 1.00 |
| | Mica | 1.00 |
| G | Water | 29.20 |
| | Butylene Glycol | 2.00 |
| | Magnesium Sulfate | 0.60 |
| | Methylparaben | 0.20 |
| | Phenoxyethanol | 0.60 |
| | Total: | 100.00 |

To prepare this composition, phase A was heated at a temperature of 80 to 85° C. for 15 minutes or until the structuring polymer Uniclear was dissolved. Phase B was added and pigment was ground under high sheer to good dispersion. Phases C, D, E and F were added sequentially while mixing. Phase G was added slowly at a temperature of 70 to 75° C. under homogenization to form emulsion. This make up composition had a silky feel.

Example 4

Anhydrous Compact Formula

| Phase | Ingredients | % W/W |
|---|---|---|
| A | Structuring polymer Uniclear 100 | 15.0 |
| | Octyldodecanol | 10.0 |
| | C12-C15 Benzoate | 16.0 |
| | Ethylhexyl Methoxycinnamate | 6.0 |
| | Isononyl Isononanoate | 7.0 |
| | PEG-30 Dipolyhydroxystearate | 2.0 |
| B | Pigment | 12.0 |
| C | Dimethicone DC 200 fluid | 12.0 |
| | Vinyl dimethicone/methicone silsesquioxane crosspolymer | 6.0 |
| D | Butylparaben | 0.5 |
| | Disteardimonium Hectorite | 0.5 |
| E | MMA Crosspolymer | 5.0 |
| | PTFE | 2.0 |
| | Nylon-12 | 3.0 |
| | Mica | 3.0 |

To prepare this composition, phase A was heated at a temperature of 80 to 85° C. for 15 minutes or until the structuring polymer was dissolved. Phase B was added and the pigments were ground under high sheer to good dispersion. Phases C, D and E were added sequentially, while mixing well. The resulting mixture was poured while hot, i.e., at a temperature of 80-85° C. into a compact. The compact had good application, with a silky and cushion feel.

Example 5

Pressed Powder

| Ingredient | % w/w |
|---|---|
| Phase A | |
| Talc | 54.33 |
| Pigments | 8.77 |
| Zinc stearate | 4.00 |
| Fillers | 9.20 |
| KSP-104 | 10.00 |
| Silicone elastomer DC 9506 | 3.00 |
| Phase B | |
| Structuring polymer Uniclear 100 | 0.67 |
| Octyldodecanol | 2.33 |
| Preservatives | 0.70 |
| Phase C | |
| Dimethicone (DC200 10Cst) | 7.00 |

To prepare this composition, add phase A was added in a Teledyne Readco CBM (Containerized batch mixer) and mixed for 10 minutes at 5000 RPM. Phases B and C (pre-blended) were added to the module and blended for 10 minutes at 3,000 RPM. The completed mixture was passed through a grinding unit, followed by pressing at about 1,000 psi. This pressed powder had a cushiony feel and a silky feel upon application.

Example 6

Stick

| Seq | Trade Name | INCI Name | Grams |
|---|---|---|---|
| A1 | ELEFAC 1-205 | OCTYLDODECYL NEOPENTANOATE | 22.800 |
| | Wickenol 151 | ISONONYL ISONONANOATE | 20.300 |
| | Pripure 379 | SQUALANE | 4.000 |
| | Phenyltrimethicone | Phenyltrimethicone | 1.000 |
| | Lameform TGI | POLYGLYCERYL-3 DIISOSTEARATE | 2.500 |
| | Eutanol G | OCTYLDODECANOL | 0.100 |
| A2 | Uniclear 100 VG | ETHYLENEDIAMINE/STEARYL DIMER DILINOLEATE COPOLYMER | 0.100 |
| A3 | Dimethicone | Dimethicone | 9.200 |
| | KSP-100 | DIEMETHCONE/VINYL DIMETHICONE CROSS POLYMER | 4.00 |
| B1 | (See below) | Amino Acid treated pigments | 12.000 |
| B2 | | FILLERS | 9.0 |
| C | DEAWAX MH 181 | Ozokerite | 2.500 |
| | CIRE DE JOJOBA HYDROGENEE GRANULES | HYDROGENATED JOJOBA OIL | 10.000 |
| | Siliconyl Beeswax | Bis-PEG-12 DIMETHICONE BEESWAX | 2.500 |
| | | | 100.00 |

Natural Beige

Pigments in B1 Above

| B1 | NAI-C47-051-10 (white) | TITANIUM DIOXIDE (and) DISODIUM STEAROYL GLUTAMATE (and) ALUMINUM HYDROXIDE | 78.830 |
|---|---|---|---|
| | NAI-C33-8075-10 (red) | IRON OXIDES (and) DISODIUM STEAROYL GLTAMATE (and) ALUMINUM HYDROXIDE | 5.560 |
| | NAI-C33-134-10 (Black) | IRON OXIDES (and) DISODIUM STEAROYL GLUTAMATE (and) ALUMINUM HYDROXIDE | 2.630 |
| | NAI-C33-8073-10 (yellow) | IRON OXIDES (and) DISODIUM STEAROYL GLUTAMATE (and) ALUMINUM HYDROXIDE | 12.880 |
| | NAI-C43-1810-10 (blue) | ULTRAMARINES (and) DISODIUM STEAROYL GLUTAMATE (and) ALUMINUM HYDROXIDE | 0.100 |
| | | | 100.00 |

To prepare the stick, the ingredients of A1 (except for the Wickenol 151 and Eutanol G) were mixed together in a main container, followed by adding B1 and B2 along with a dispersant (Sylversone) until good pigment dispersion was achieved. The ingredients of phase A3 were then added using a mixing blade, until a homogeneous mixture was obtained. The Wickenol 151 and Eutanol G were mixed together in a separate container, followed by the addition of phase A2, with heating to 80° C. until the mixture was transparent and free of clumping. The main container was heated to a temperature of 80° C. and the contents of the separate container added thereto, followed by the addition of the ingredients of phase C. The resultant mixture was mixed until homogeneous (completely melted), and the temperature was reduced to 70-75° C. The contents were poured into molds at 70-75° C.

Example 7

Intermediate Composition

| Trade Name | Wt. % |
|---|---|
| Uniclear 100VG | 60 |
| KSP-100 | 15 |
| dimethicone | 25 |

All publications cited in the specification, both patent publications and non-patent publications, are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:

1. A cosmetic composition comprising at least one liquid fatty phase comprising: at least one structuring agent comprising a polymer skeleton having a hydrocarbon-based repeating unit comprising at least one hetero atom; a silicone elastomer powder comprising a silicone elastomer core coated with a silicone resin; and at least one swelling agent for said powder.

2. The cosmetic composition of claim 1, wherein said at least one structuring agent further comprises at least one fatty chain bonded to said polymer skeleton.

3. The cosmetic composition of claim 2, wherein said at least one fatty chain is a pendant chain.

4. The cosmetic composition of claim 2, wherein said at least one fatty chain is a terminal chain.

5. The cosmetic composition of claim 4, wherein said at least one fatty chain is bonded to said polymer skeleton via an ester group.

6. The cosmetic composition of claim 2, wherein said at least one structuring agent comprises a plurality of fatty chains, including a terminal fatty chain.

7. The cosmetic composition of claim 2, wherein said at least one fatty chain is functionalized.

8. The cosmetic composition of claim 1, wherein said polymer skeleton is a polyamide.

9. The cosmetic composition of claim 8, wherein said at least one structuring agent is chosen from polyamide polymers of formula (I):

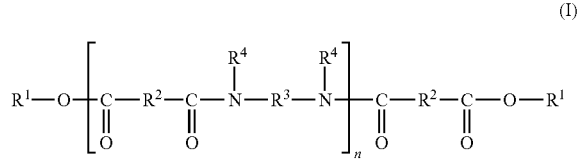

wherein:
- n is an integer which represents the number of amide units such that the number of ester groups present in said at least one polyamide polymer ranges from 10% to 50% of the total number of all ester groups and all amide groups comprised in said at least one polyamide polymer;
- $R^1$, which are identical or different, are each chosen from alkyl groups comprising at least 4 carbon atoms and alkenyl groups comprising at least 4 carbon atoms;
- $R^2$, which are identical or different, are each chosen from $C_4$ to $C_{42}$ hydrocarbon-based groups with the proviso that at least 50% of all $R^2$ are chosen from $C_{30}$ to $C_{42}$ hydrocarbon-based groups;
- $R^3$, which are identical or different, are each chosen from organic groups comprising atoms chosen from carbon atoms, hydrogen atoms, oxygen atoms and nitrogen atoms, with the proviso that $R^3$ comprises at least 2 carbon atoms; and
- $R^4$, which are identical or different, are each chosen from hydrogen atoms, $C_1$ to $C_{10}$ alkyl groups and a direct bond to at least one group chosen from $R^3$ and another $R^4$ such that when said at least one group is chosen from another $R^4$, the nitrogen atom to which both $R^3$ and $R^4$ are bonded forms part of a heterocyclic structure defined in part by $R^4$—N—$R^3$, with the proviso that at least 50% of all $R^4$ are chosen from hydrogen atoms.

10. The cosmetic composition of claim 1, wherein said at least one swelling agent is chosen from linear and cyclic polydimethylsiloxanes.

11. The cosmetic composition of claim 10, wherein said cyclic polydimethylsiloxanes are chosen from cyclomethicones.

12. The cosmetic composition of claim 10, wherein said linear polydimethylsiloxanes are chosen from dimethicones.

13. The cosmetic composition of claim 1, wherein said at least one swelling agent is chosen from phenylmethicones.

14. The cosmetic composition of claim 1, wherein said at least one swelling agent is chosen from fluorinated silicones.

15. The cosmetic composition of claim 1, wherein said silicone resin comprises a polyorganosilsesquioxane.

16. The cosmetic composition of claim 1, wherein said silicone elastomer core is unfunctionalized.

17. The cosmetic composition of claim 1, wherein said silicone elastomer core contains pendant functional groups.

18. The cosmetic composition of claim 17, wherein said functional groups comprise fluoroalkyl groups.

19. The cosmetic composition of claim 17, wherein said functional groups comprise phenyl groups.

20. The cosmetic composition of claim 1, wherein said at least one structuring agent comprises a polyamide bonded to a fatty chain via an ester group, said at least one swelling agent is chosen from dimethicones, and said silicone resin comprises a polyorganosilsesquioxane.

21. The cosmetic composition of claim 1, wherein said at least one liquid fatty phase is chosen from polar oils, apolar oils, and mixtures thereof.

22. The cosmetic composition of claim 1, which is in the form of an emulsion.

23. The cosmetic composition of claim 22, further comprising an aqueous phase.

24. The cosmetic composition of claim 22, which is anhydrous.

25. The cosmetic composition of claim 1, further comprising at least one film-forming agent.

26. The cosmetic composition of claim 1, further comprising at least one wax.

27. The cosmetic composition of claim 1, further comprising at least one sunscreen agent.

28. The cosmetic composition of claim 1, further comprising at least one emulsifier.

29. The cosmetic composition of claim 1, further comprising at least one plasticizer.

30. The cosmetic composition of claim 1, further comprising at least one additive.

31. The cosmetic composition of claim 30, wherein the at least one additive is at least one pigment.

32. The cosmetic composition of claim 31, wherein said at least one pigment is treated.

33. The cosmetic composition of claim 31, wherein said at least one pigment is treated with an amino acid.

34. The cosmetic composition of claim 1, which is in the form of a solid, a paste, a gel or a cream.

35. The cosmetic composition of claim 1, which is in a molded form.

36. The cosmetic composition of claim 1, which is in the form of a stick or dish.

37. The cosmetic composition of claim 1, which is in the form of a powder.

38. A method for care, make-up or treatment of a keratin material, comprising applying to the keratin material a cosmetic composition comprising an anhydrous emulsion comprising at least one liquid fatty phase comprising: at least one structuring agent comprising a polymer skeleton having a hydrocarbon-based repeating unit comprising at least one hetero atom; a silicone elastomer powder comprising a silicone elastomer core coated with a silicone resin; and at least one swelling agent for the powder.

39. The method of claim 38, wherein the keratin material comprises lips.

40. The method of claim 38, wherein the keratin material comprises skin.

41. The method of claim 38, wherein the keratin material comprises keratinous fibers.

42. The method of claim 38, wherein the at least one structuring agent is chosen from a polyamide bonded to a fatty chain via an ester group, the at least one swelling agent is chosen from dimethicones, and the silicone resin comprises a polyorganosilsesquioxane.

43. The cosmetic composition of claim 1, wherein the at least one structuring agent is chosen from ethylenediamine/stearyl dimer dilinoleate copolymer.

44. The method of claim 38, wherein the at least one structuring agent is chosen from ethylenediamine/stearyl dimer dilinoleate copolymer.

45. A cosmetic composition comprising: at least one liquid fatty phase comprising at least one structuring agent comprising a polymer skeleton having a hydrocarbon-based repeating unit comprising at least one hetero atom; a silicone elastomer powder comprising a silicone elastomer core coated with a silicone resin; and at least one swelling agent for said powder; wherein said at least one structuring agent is chosen from polyamide polymers of formula (I):

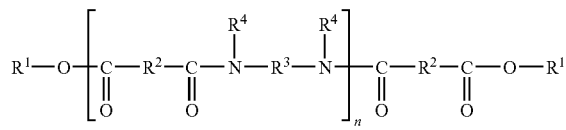

wherein:
- n is an integer which represents the number of amide units such that the number of ester groups present in said at least one polyamide polymer ranges from 10% to 50% of the total number of all ester groups and all amide groups comprised in said at least one polyamide polymer;
- $R^1$, which are identical or different, are each chosen from alkyl groups comprising at least 4 carbon atoms and alkenyl groups comprising at least 4 carbon atoms;
- $R^2$, which are identical or different, are each chosen from $C_4$ to $C_{42}$ hydrocarbon-based groups with the proviso that at least 50% of all $R^2$ are chosen from $C_{30}$ to $C_{42}$ hydrocarbon-based groups;
- $R^3$, which are identical or different, are each chosen from organic groups comprising atoms chosen from carbon atoms, hydrogen atoms, oxygen atoms and nitrogen atoms, with the proviso that $R^3$ comprises at least 2 carbon atoms; and
- $R^4$, which are identical or different, are each chosen from hydrogen atoms, $C_1$ to $C_{10}$ alkyl groups and a direct bond to at least one group chosen from $R^3$ and another $R^4$ such that when said at least one group is chosen from another $R^4$, the nitrogen atom to which both $R^3$ and $R^4$ are bonded forms part of a heterocyclic structure defined in part by $R^4$—N—$R^3$, with the proviso that at least 50% of all $R^4$ are chosen from hydrogen atoms.

46. The cosmetic composition of claim 45, wherein said at least one swelling agent is chosen from linear and cyclic polydimethylsiloxanes.

47. The cosmetic composition of claim 46, wherein said cyclic polydimethylsiloxanes are chosen from cyclomethicones.

48. The cosmetic composition of claim 46, wherein said linear polydimethylsiloxanes are chosen from dimethicones.

49. The cosmetic composition of claim 45, wherein said at least one swelling agent is chosen from phenylmethicones.

50. The cosmetic composition of claim 45, wherein said at least one swelling agent is chosen from fluorinated silicones.

51. The cosmetic composition of claim 45, wherein said silicone resin comprises a polyorganosilsesquioxane.

52. The cosmetic composition of claim 45, wherein said silicone elastomer core is unfunctionalized.

53. The cosmetic composition of claim 45, wherein said silicone elastomer core contains pendant functional groups.

54. The cosmetic composition of claim 45, wherein said functional groups comprise fluoroalkyl groups.

55. The cosmetic composition of claim 53, wherein said functional groups comprise phenyl groups.

56. The cosmetic composition of claim 55, wherein said at least one structuring agent comprises a polyamide bonded to a fatty chain via an ester group, said at least one swelling agent is chosen from dimethicones, and said silicone resin comprises a polyorganosilsesquioxane.

57. The cosmetic composition of claim 45, wherein said at least one liquid fatty phase is chosen from polar oils, apolar oils, and mixtures thereof.

58. The cosmetic composition of claim 45, which is in the form of an emulsion.

59. The cosmetic composition of claim 58, further comprising an aqueous phase.

60. The cosmetic composition of claim 58, which is anhydrous.

61. The cosmetic composition of claim 45, further comprising at least one film-forming agent.

62. The cosmetic composition of claim 45, further comprising at least one wax.

63. The cosmetic composition of claim 45, further comprising at least one sunscreen agent.

64. The cosmetic composition of claim 45, further comprising at least one emulsifier.

65. The cosmetic composition of claim 45, further comprising at least one plasticizer.

66. The cosmetic composition of claim 45, further comprising at least one additive.

67. The cosmetic composition of claim 66, wherein the at least one additive is at least one pigment.

68. The cosmetic composition of claim 67, wherein said at least one pigment is treated.

69. The cosmetic composition of claim 67, wherein said at least one pigment is treated with an amino acid.

70. The cosmetic composition of claim 45, which is in the form of a solid, a paste, a gel or a cream.

71. The cosmetic composition of claim 45, which is in a molded form.

72. The cosmetic composition of claim 45, which is in the form of a stick or dish.

73. The cosmetic composition of claim 45, which is in the form of a powder.

74. A method for care, make-up or treatment of a keratin material, comprising applying to the keratin material a cosmetic composition comprising an anhydrous emulsion comprising: at least one liquid fatty phase comprising at least one structuring agent comprising a polymer skeleton having a hydrocarbon-based repeating unit comprising at least one hetero atom; a silicone elastomer powder comprising a silicone elastomer core coated with a silicone resin; and at least one swelling agent for the powder; wherein said at least one structuring agent is chosen from polyamide polymers of formula (I):

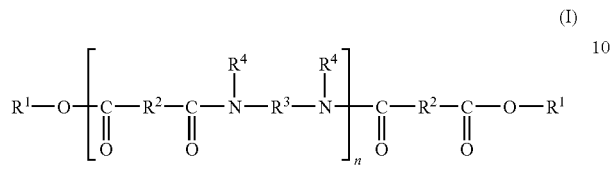

wherein:
- n is an integer which represents the number of amide units such that the number of ester groups present in said at least one polyamide polymer ranges from 10% to 50% of the total number of all ester groups and all amide groups comprised in said at least one polyamide polymer;
- $R^1$, which are identical or different, are each chosen from alkyl groups comprising at least 4 carbon atoms and alkenyl groups comprising at least 4 carbon atoms;
- $R^2$, which are identical or different, are each chosen from $C_4$ to $C_{42}$ hydrocarbon-based groups with the proviso that at least 50% of all $R^2$ are chosen from $C_{30}$ to $C_{42}$ hydrocarbon-based groups;
- $R^3$, which are identical or different, are each chosen from organic groups comprising atoms chosen from carbon atoms, hydrogen atoms, oxygen atoms and nitrogen atoms, with the proviso that $R^3$ comprises at least 2 carbon atoms; and
- $R^4$, which are identical or different, are each chosen from hydrogen atoms, $C_1$ to $C_{10}$ alkyl groups and a direct bond to at least one group chosen from $R^3$ and another $R^4$ such that when said at least one group is chosen from another $R^4$, the nitrogen atom to which both $R^3$ and $R^4$ are bonded forms part of a heterocyclic structure defined in part by $R^4$—N—$R^3$, with the proviso that at least 50% of all $R^4$ are chosen from hydrogen atoms.

75. The method of claim 74, wherein the keratin material comprises lips.

76. The method of claim 74, wherein the keratin material comprises skin.

77. The method of claim 74, wherein the keratin material comprises keratinous fibers.

78. The method of claim 74, wherein the at least one structuring agent is chosen from a polyamide bonded to a fatty chain via an ester group, the at least one swelling agent is chosen from dimethicones, and the silicone resin comprises a polyorganosilsesquioxane.

79. The cosmetic composition of claim 53, wherein the at least one structuring agent is chosen from ethylenediamine/stearyl dimer dilinoleate copolymer.

* * * * *

UNITED STATES PATENT AND TRADEMARK OFFICE
CERTIFICATE OF CORRECTION

PATENT NO. : 7,749,524 B2 Page 1 of 1
APPLICATION NO. : 10/746612
DATED : July 6, 2010
INVENTOR(S) : Shao Xiang Lu et al.

It is certified that error appears in the above-identified patent and that said Letters Patent is hereby corrected as shown below:

In claim 54, col. 28, line 19, "The cosmetic composition of claim 45" should read --The cosmetic composition of claim 53--.

In claim 56, col. 28, line 23, "The cosmetic composition of claim 55" should read --The cosmetic composition of claim 45--.

Signed and Sealed this

Twenty-first Day of September, 2010

David J. Kappos
*Director of the United States Patent and Trademark Office*